(12) United States Patent
Mayor Menéndez et al.

(10) Patent No.: US 9,096,554 B2
(45) Date of Patent: Aug. 4, 2015

(54) DRUGS FOR INHIBITING P38 AND USES THEREOF

(71) Applicant: UNIVERSIDAD AUTÓNOMA DE MADRID, Madrid (ES)

(72) Inventors: Federico Mayor Menéndez, Madrid (ES); Cristina Murga Montesinos, Madrid (ES); Pedro Manuel Campos Muelas, Madrid (ES); Jacoba Johana Heijnen, Madrid (ES); Anna Maria Agnes Antonius Kavelaars, Madrid (ES); Antonio Morreale de León, Madrid (ES); Rubén Gil Redondo, Madrid (ES)

(73) Assignee: UNIVERSIDAD AUTÓNOMA DE MADRID, Madrid (ES)

( * ) Notice: Subject to any disclaimer, the term of this patent is extended or adjusted under 35 U.S.C. 154(b) by 0 days.

(21) Appl. No.: 14/355,545

(22) PCT Filed: Oct. 31, 2012

(86) PCT No.: PCT/ES2012/070762
§ 371 (c)(1),
(2) Date: Apr. 30, 2014

(87) PCT Pub. No.: WO2013/064714
PCT Pub. Date: May 10, 2013

(65) Prior Publication Data
US 2014/0296308 A1    Oct. 2, 2014

(30) Foreign Application Priority Data
Nov. 2, 2011   (ES) .................................. 201131754

(51) Int. Cl.
C07D 271/12    (2006.01)
A61K 31/4245    (2006.01)

(52) U.S. Cl.
CPC .......... *C07D 271/12* (2013.01); *A61K 31/4245* (2013.01)

(58) Field of Classification Search
CPC ........................... C07D 271/12; A61K 31/4245
See application file for complete search history.

(56) References Cited

U.S. PATENT DOCUMENTS

| 2005/0282818 A1 | 12/2005 | Ramesh et al. |
| 2008/0039461 A1 | 2/2008 | Protter et al. |
| 2009/0074676 A1 | 3/2009 | Yang |
| 2010/0099683 A1 | 4/2010 | Tomkinson et al. |

FOREIGN PATENT DOCUMENTS

| WO | WO 00/42022 | 7/2000 |
| WO | WO 01/05390 | 1/2001 |
| WO | WO 2004/004725 | 1/2004 |
| WO | WO 2004/014387 | 2/2004 |
| WO | WO 2004/021988 | 3/2004 |
| WO | WO 2005/032551 | 4/2005 |
| WO | WO 2006/002284 | 1/2006 |
| WO | WO 2009/074676 | 6/2009 |
| WO | WO 2010/083404 | 7/2010 |
| WO | WO 2010/128156 | 11/2010 |
| WO | WO 2013/064714 | 5/2013 |

OTHER PUBLICATIONS

Berque-Bestel et al. J. Med. Chem. 2003, 46, 2606-2620.*
CAS Registry No. 413612-01-8, which entered STN on May 12th, 2002.*
Munoz et al. Neuropharmacology 2010, 58, 561-568.*
Cuenda et al. Biochimica et Biophysica Acta 2007, 1773, 1358-1375.*
Martin et al. Drug Discovery Today: Therapeutic Strategies 2012, 9, e183-e188.*
Mavropoulos et al. Autoimmunity Reviews 2013, 12, 580-590.*
Hussain et al. Diabetes Research and Clinical Practice 2007, 76, 317-326.*
Du et al. JOVS 2010, 51, 2158-2164.*
Luo et al. Cell, 2009, 136, pp. 823-837.*
Hill et al. JPET 2008, 327, 610-616.*
Krementsov et al. Molecular and Cellular Biology 2013, 33, 3728-3734.*
Bendotti et al. Central Nervous System Agents in Medicinal Chemistry, 2006, 6, 1-9.*
Emory University Molecular Libraries Screening Center, HTS for 14-3-3 protein interaction modulators, PubChem BioAssay AID 422, Deposit Date Jun. 22, 2006, access date Mar. 26, 2015, obtained from http://pubchem.ncbi.nlm.nih.gov/assay/assay.cgi?aid=422.*
PubChem Entry for CID 2836609, Create Date Jul. 28, 2005, Access Date Mar. 25, 2015, obtained from http://pubchem.ncbi.nlm.nih.gov/compound/2836609.*
Evgen'ev et al. Journal of Analytical Chemistry 2011, 66, 585-589.*
Dewil et al., "Inhibition of p38 mitogen activated protein kinase activation and mutant SOD1$^{G93A}$-induced motor neuron death," Neurobiology of Disease, vol. 26, pp. 332-341 (2007).
International Search Report corresponding to International Application No. PCT/ES2012/070762 dated Aug. 2, 2013.

(Continued)

*Primary Examiner* — Matthew Coughlin

(74) *Attorney, Agent, or Firm* — Jenkins, Wilson, Taylor & Hunt, P.A.

(57) ABSTRACT

The present invention relates to compounds with a benzoxadiazolyl amine structure which are capable of inhibiting the activation or the biological activity of p38 mitogen-activated protein kinase (MAPK) and the use thereof in the treatment of a disease that can be alleviated by means of inhibiting the activation or the biological activity of said p38 MAPK, for example, an inflammatory disease or a disease presenting with pain.

9 Claims, 12 Drawing Sheets

(56) References Cited

OTHER PUBLICATIONS

Kamiska, "MAPK signalling pathways as molecular targets for anti-inflammatory therapy—from molecular mechanisms to therapeutic benefits" Biochimica et Biophysica Acta, vol. 1754, pp. 253-262 (2005).

Notification concerning Transmittal of International Preliminary Report on Patentability corresponding to International Application No. PCT/ES2012/070762 dated May 15, 2014.

Yasuda et al., "p38 MAP Kinase Inhibitors as Potential Therapeutic Drugs for Neural Diseases" Central Nervous System Agents in Medicinal Chemistry, vol. 11, No. 1 pp. 45-59 (2011).

European Search Report corresponding to Application No. 12846045.8-1462 dated Mar. 19, 2015.

Evgen'ev et al., "Efficiency of Separating Amnie 5,7-Dinitrobenzofurazane Derivatives," Journal of Analytical Chemistry, vol. 66, No. 7, pp. 585-589 (2011).

* cited by examiner

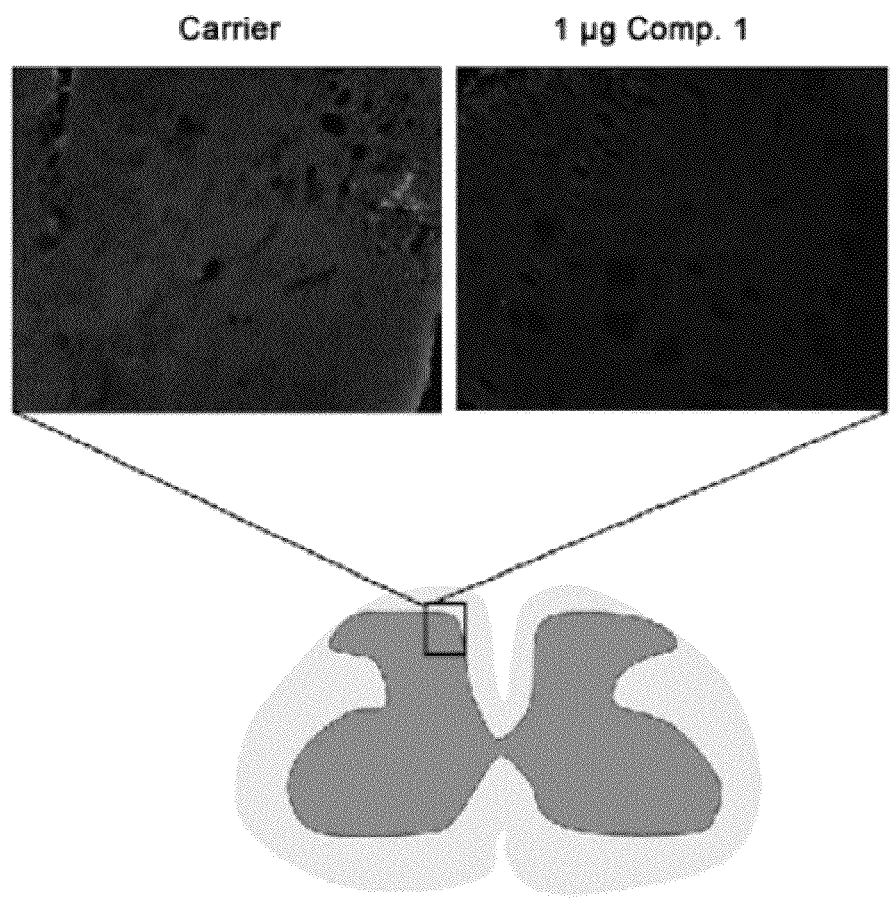
FIG. 11C
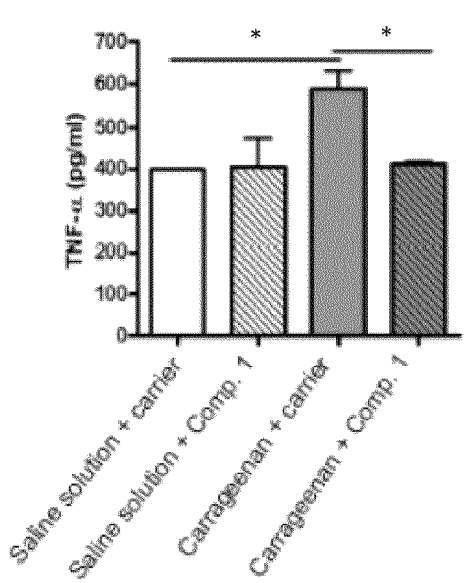
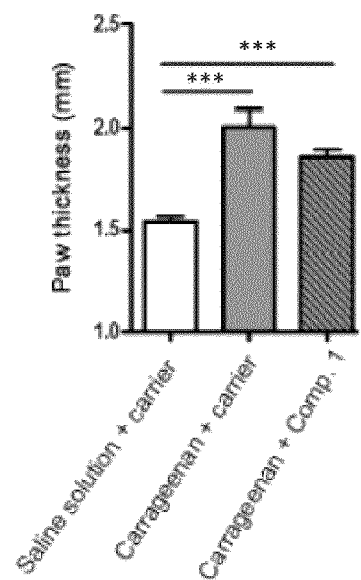
FIG. 11D                    FIG. 11E

DRUGS FOR INHIBITING P38 AND USES THEREOF

CROSS-REFERENCE TO RELATED APPLICATIONS

This application is filed under the provisions of 35 U.S.C. §371 and claims the priority of International Patent Application No. PCT/ES2012/070762 filed on Oct. 31, 2012, and of Spanish Patent Application No. P201131754 filed on Nov. 2, 2011.

FIELD OF THE INVENTION

The present invention generally relates to compounds with a benzoxadiazolyl amine structure, compositions comprising said compounds and the use thereof for inhibiting the activation or the biological activity of p38 mitogen-activated protein kinase (MAPK).

BACKGROUND OF THE INVENTION p38 protein kinase is a member of a family of signaling molecules known as the mitogen-activated protein kinase (MAPK) family, a family of Ser/Thr kinases which are responsible for a number of cell processes such as cell growth, proliferation, cell death and differentiation in response to a wide range of stimuli. The p38 subfamily responds to a number of stress stimuli, for example, ultraviolet light, osmotic shock, heat, and inflammatory cytokines such as tumor necrosis factor alpha (TNF-α) and interleukin-1 beta (IL-1β).

p38 MAPK plays an important role in very diverse processes, such as in inflammation, cell differentiation (for example, myoblast-myotube conversion, preadipocyte cell differentiation, thymocyte differentiation, etc.), in the regulation of cell migration in response to various stimuli (for example, endothelial cell migration stimulated by endothelial growth factor (VEGF), etc.), and in cell cycle (in which the p38-MK2 pathway regulates the G2/M checkpoint in response to ultraviolet light or the G0 and G1/S checkpoints).

p38 MAPK pathway dysfunction has been correlated with the etiology and/or development of various pathologies, among which rheumatoid arthritis, psoriasis, heart failure, diabetes and even Alzheimer's disease are found. Recently, the role of p38 MAPK has been linked particularly to multiple sclerosis (MS) and amyotrophic lateral sclerosis (ALS). p38 MAPK has therefore become an important therapeutic target. By way of illustration, the use of various p38 MAPK inhibitors has been described in the treatment of respiratory diseases (EP 1534282), autoimmune diseases such as rheumatoid arthritis, psoriasis or Crohn's disease (WO 2004/014387), pain (WO 2004/021988, US2008/0039461), cardiovascular diseases (WO 2005/032551) and in weight loss or the treatment of obesity (US2009/0074676). In a general review of p38 MAPK inhibitors and their effects on inflammation, B. Kamiska (Kamiska B., Biochimica et Biophysica Acta, 2005, 1754, 253-262) describes the inhibitory effect of compound SB 203580 [4-[4-(4-fluorophenyl)-2-(4-(methylsulfinylphenyl)-1H-imidazol-5-yl]pyridine], which is potentially useful as an anti-inflammatory agent in the treatment of rheumatoid arthritis, on p38 MAPK.

With respect to the role of p38 MAPK in multiple sclerosis (MS), Yasuda et al. (Yasuda et al., Cent New Syst Agents Med Chem., 2011, 11(1):45) describe that activation of the p38 cascade releases proinflammatory cytokines which are linked to this disease as well as to cerebral ischemia, Alzheimer's disease and Parkinson's disease. This study also describes new p38 MAPK inhibitors that are in phase II for the treatment of neuropathic pain and depression. p38α and p38β are known to be expressed in the brain and frequently activated in animal models of neurodegeneration, giving rise to the disturbance of physiological properties, activation of response genes and neurotoxicity (Harper et al., Expert Opin. Ther. Targets, 2003, 7: 187). The studies by Guo and Coulthard (Guo and Baht, Neurochemical Research, 2007, 32 (12) 2160; Coulthard et al., Trends in Mo. Med., 2009, 15(8):369) establish that the neuroprotective function of minocycline in animal models of MS and ischemia can be partly attributed to the inhibition of p38 MAPK signaling. On the other hand, the activation of p38 MAPK is necessary for the development and progression of chronic experimental allergic encephalomyelitis (EAE) and the relapsing-remitting course and the inhibition of p38 MAPK activity in T-cells is enough to modulate the severity of EAE (Noubade et al., Blood, 2011, 118(12): 3290). Oral treatment with an ASK1 (p38 cascade activator) inhibitor suppressed EAE-induced inflammation in the spinal cord and in optic nerves (Guo et al., EMBO Mol Med, 2010, 2, 12:504) which corroborates the TLR-ASK1-p38 pathway in glial cells as a therapeutic target for demyelinating disorders such as multiple sclerosis.

With respect to the role of p38 MAPK in amyotrophic lateral sclerosis (ALS), the relationship between the aberrant expression of p38 MAPK and its activation in motor neurons and microglia for ALS progression must be highlighted (Bendotti et al., Neurodegener. Dis., 2005, 128). Furthermore, the continuous activation of p38 is correlated with motor neuron degeneration in transgenic mouse models of ALS (SOD1 mutant G93A) (Tortarolo M et al., Mol Cell Neurosci., 2003, 23(2); Holasek et al., Brain Res., 2005 1045:185), whereas a p38 MAPK inhibitor (SB203580) prevents SOD1 mutant-induced apoptosis of motor neurons (Dewil et al., Neurobiol. Dis., 2007, 26: 332). It has also been described that both p38 and JNK1 are involved in cytoskeletal abnormalities of spinal motor neurons, a characteristics of familial and sporadic ALS, through the aberrant phosphorylation and subsequent aggregation of neurofilaments (Bendotti et al., J. Neuropathol. Exp. Neurol., 2004, 63: 113; Ackerley et al., Mol. Cell. Neurosci., 2004, 26:354; Brownlees et al., J. Cell Sci., 2000 113: 401).

Although p38 MAPK inhibitors have been described, there is still a need to identify new compounds for inhibiting said kinase that are potentially useful in human therapy for the purpose of increasing the range of therapeutic approaches against p38 MAPK-regulated diseases that can be alleviated by means of inhibiting the biological activity of said p38 MAPK, particularly diseases presenting with local neuroinflammation or pain.

Document US 2005/0282818 describes heterocyclic compounds for inhibiting ubiquitin ligase, where said compounds are described as potentially useful for (indirectly) regulating the activity of MAP kinases. These compounds include molecules with a benzoxadiazolyl phenyl amine structure.

Document WO 2010/083404 relates to various benzoxadiazoles that are capable of interfering with Myc and Max association and are therefore potentially useful in the treatment of proliferative diseases.

Document US 2010/0099683 relates to the use of DNA ligase inhibitors for the treatment of cancer, among which inhibitors some derivatives with a benzoxadiazole structure are found.

Documents WO 2001/05390 and WO 2000/042022 describe compounds for inhibiting MEK kinase for the treatment of chronic pain and proliferative diseases, respectively.

These documents include examples with a benzoxadiazole structure substituted with a group derived from carboxylic acid.

BRIEF DESCRIPTION OF THE INVENTION

The invention relates to compounds with a benzoxadiazolyl phenyl amine structure that are capable of inhibiting p38 MAPK. Furthermore, various assays performed by the inventors have clearly shown that compounds with a benzo[1,2,5]oxadiazolyl phenyl amine structure which are substituted at least in positions 2 and 5 of the phenyl ring have greater activity as p38 kinase inhibitors compared to compounds having another substitution pattern.

Therefore, in a first aspect, the invention relates to the use of a compound of formula (I):

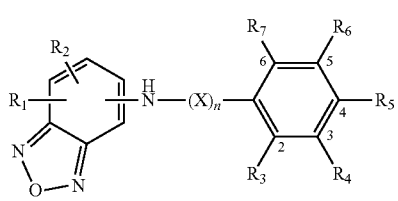

(I)

where
n represents 0 or 1;
X represents —$CH_2$— or —C(O)—;
$R_1$ and $R_2$ are independently selected from the group consisting of H, halogen, $NO_2$, $CF_3$ and CN;
$R_3$ and $R_6$ are independently selected from the group consisting of halogen, OH, optionally substituted $C_1$-$C_6$ alkyl, optionally substituted $C_1$-$C_6$ alkoxy, $C_{1-6}$ haloalkyl, $NH_2$, $NO_2$ and CN;
$R_4$, $R_5$ and $R_7$ are independently selected from the group consisting of H, halogen, OH, optionally substituted $C_1$-$C_6$ alkyl, optionally substituted $C_1$-$C_6$ alkoxy, $C_{1-6}$ haloalkyl, $NH_2$, $NO_2$ and CN;
or a salt or solvate thereof,
in the preparation of a medicinal product.

In another aspect, the invention relates to the compound of formula (I), or a salt or solvate thereof, for use in the preparation of a medicinal product.

In another aspect, the invention relates to the use of a compound of formula (I), or a salt or solvate thereof, in the preparation of a medicinal product for the prevention and/or treatment of a p38 MAPK-regulated disease, such as a disease that can be alleviated by means of inhibiting the activation or the biological activity of said p38 MAPK.

In another aspect, the invention relates to the compound of formula (I), or a salt or solvate thereof, for use in the prevention and/or treatment of a p38 MAPK-regulated disease, such as a disease that can be alleviated by means of inhibiting the activation or the biological activity of said p38 MAPK.

In another aspect, the invention relates to a pharmaceutical composition comprising a compound of formula (I), or a salt or solvate thereof, and a pharmaceutically acceptable carrier.

In another aspect, the invention relates to a compound of formula (I) as defined above, with the proviso that the compound of formula (I) is not (5-chloro-2-methyl-phenyl)-(7-chloro-4-nitro-benzo[1,2,5]oxadiazol-5-yl)-amine (Compound 5) or (7-chloro-4-nitro-benzo[1,2,5]oxadiazol-5-yl)-(2,5-dimethyl-phenyl)-amine (Compound 6).

In another aspect, the invention relates to a method for preparing a compound of formula (I), or a salt or solvate thereof.

In another aspect, the invention relates to a method of treating a p38 MAPK-regulated disease, which comprises administering to a patient a therapeutically effective amount of at least one compound of formula (I), or a salt or solvate thereof.

BRIEF DESCRIPTION OF THE DRAWINGS

FIG. 9B shows that the lowest effective dose in LysM-GRK2$^{f/+}$ mice is 0.5 μg of Compound 1.

FIG. 11C shows the sections of the isolated spinal cord two days after treatment with 1 μg of Compound 1 stained with Fluoro-Jade B.

FIG. 11D shows TNF-α levels in the spinal cord two days after treatment with Compound 1. TNF-α levels were determined in spinal cord lysates with an anti-TNF ELISA kit and the mean±SEM (n=4) is plotted on a graph, a significant reduction of TNF-α levels by Compound 1 being observed, not being significantly different from the inflammation obtained with carrageenan plus carrier, which indicates that treatment with Compound 1 does not directly affect peripheral inflammatory activity.

FIG. 11E shows a measurement of ongoing inflammation, measuring the thickness of the paw of the mouse (n=8) six days after treatment with Compound 1.

DETAILED DESCRIPTION OF THE INVENTION

Figure 1:
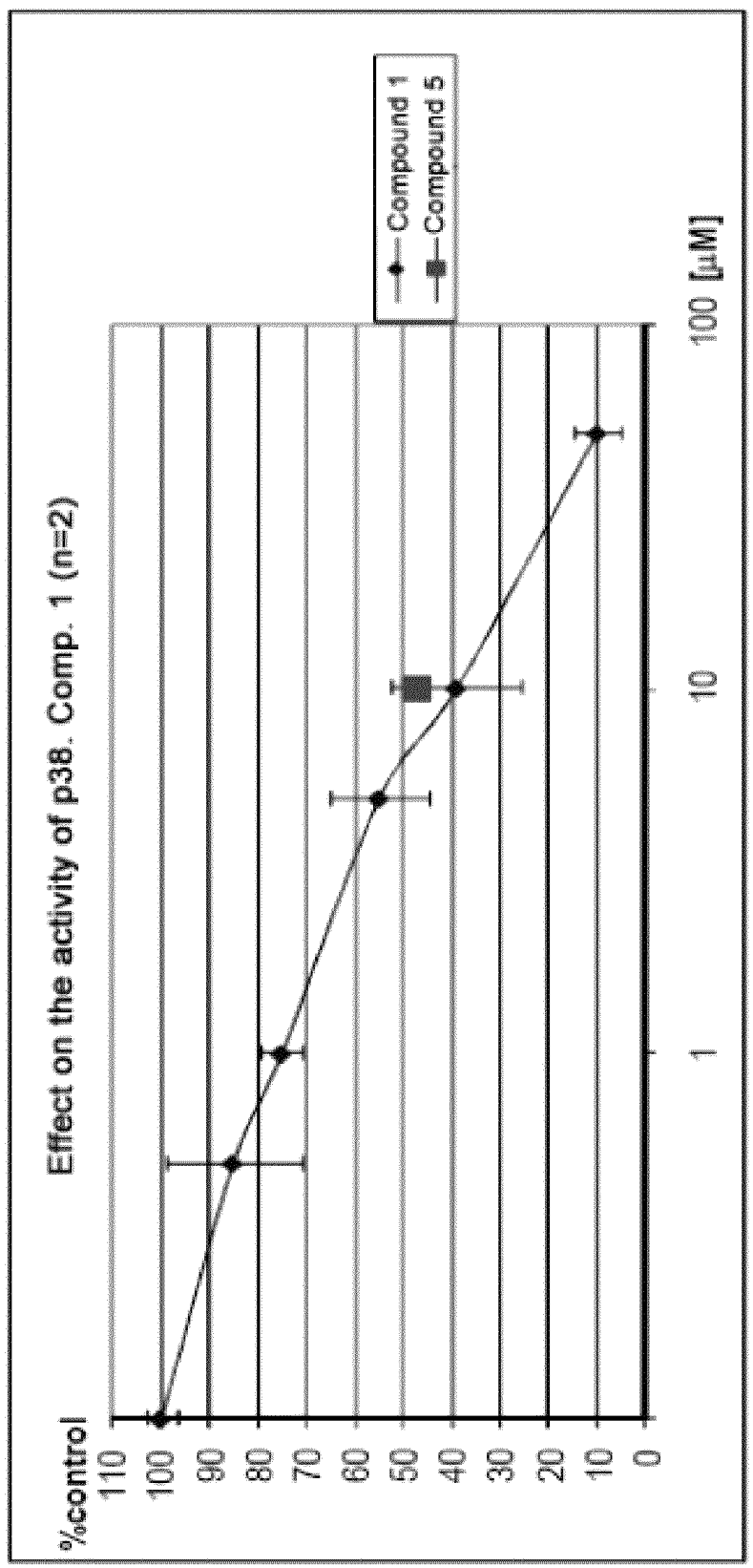
FIG. 1 shows the inhibitory effect of Compound 1 on the activity of p38 MAPK. After in vitro phosphorylation of the substrate MEF2A by purified recombinant p38 in the presence of different concentrations of Compound 1 (or 10 µM of Compound 5 used as control), the proteins were resolved by means of SDS-PAGE and the degree of MEF2A phosphorylation was quantified after Western Blot with specific antibodies. The means of the results of two independent experiments conducted in duplicate are graphically depicted in percentage with respect to the controls with DMSO.

In the context of the present invention, the following terms have the meaning detailed below:

The term "$C_{1-6}$ alkyl" refers to an aliphatic linear or branched chain radical that has between 1 and 6, preferably between 1 and 3 ("$C_{1-3}$ alkyl"), carbon atoms and is bound to the remaining molecule by means of a single bond. This term includes, for example and in a non-limiting manner, methyl, ethyl, n-propyl, i-propyl, n-butyl, t-butyl, n-pentyl, etc.

The term "$C_{1-6}$ haloalkyl" refers to an alkyl radical as defined above where at least one hydrogen atom has been replaced with a halogen atom. This term includes, for example and in a non-limiting manner, fluoromethyl, bromomethyl, iodomethyl, difluoromethyl, trifluoromethyl, 2-fluoroethyl, 2-chloroethyl, 1-fluoroethyl, pentafluoroethyl, 1-fluoropropyl, 2-chloropropyl, 3-fluoropropyl, 3-chloropropyl, 1-fluorobutyl, 1-chlorobutyl, 4-fluorobutyl. Haloalkyl is preferably $CF_3$.

The term "alkoxy $C_{1-6}$" refers to an —O-alkyl group, where alkyl is as defined above. Alkoxy is preferably methoxy.

The term "halogen" refers to bromine, chlorine, iodine or fluorine. Halogen is preferably fluorine or chlorine.

The term "cycloalkyl" refers to a saturated or partially saturated mono- or polycyclic aliphatic group that has between 3 and 10, preferably between 3 and 6, carbon atoms and is bound to the remaining molecule by means of a single bond, including, for example and in a non-limiting manner, cyclopropyl, cyclobutyl, cyclohexyl, cyclopentyl, etc.

The term "aryl" refers to an aromatic group that has between 6 and 18, preferably between 6 and 10, even more preferably 6 or 10, carbon atoms, comprising 1, 2 or 3 aromatic nuclei bound by means of a carbon-carbon bond or by condensing, including, for example and in a non-limiting manner, phenyl, naphthyl, diphenyl, indenyl, phenanthryl, etc.

"Heterocycle" refers to a 3- to 10-membered stable ring radical, preferably a 5- or 6-membered ring, which consists of carbon atoms and from one to five heteroatoms selected from the group consisting of nitrogen, oxygen and sulfur and which can be partially or completely saturated or can be aromatic ("heteroaryl"). For the purposes of this invention, the heterocycle can be a monocyclic, bicyclic or tricyclic ring system which can include condensed ring systems. The examples of such heterocycles include, but are not limited to, pyrrolidine, piperidine, piperazine, morpholine, tetrahydrofuran, benzimidazole, benzothiazole, furan, pyrrole, pyridine, pyrimidine, isothiazole, imidazole, indole, purine, quinoline, thiadiazole.

As is understood in this technical field, there can be a certain degree of substitution in the radicals defined above. With respect to the substituted groups, the references of the present document indicate that the specified radical can be substituted in one or more available positions with one or more substituents. Said substituents include, for example and in a non-limiting manner, $C_{2-6}$ alkyl, $C_{2-6}$ alkenyl, $C_{2-6}$ alkynyl, cycloalkyl, aryl, heterocycle, halogen, CN, $NO_2$, $CF_2$, —$N(R_a)(R_b)$, —OR, —$SR_d$, —$C(O)R_e$, —$C(O)OR_f$, —$C(O)N(R_g)(R_h)$, —$OC(O)R_i$; wherein $R_a$, $R_b$, $R_c$, $R_d$, $R_e$, $R_f$, $R_g$, $R_h$ and $R_i$ are independently selected from hydrogen, $C_1$-$C_6$ alkyl, aryl, heterocycle and trifluoromethyl.

The compounds of formula (I) can be in the form of salts, preferably pharmaceutically acceptable salts, and in the form of solvates. The term "pharmaceutically acceptable" preferably refers to compositions and molecular entities that are physiologically tolerable and do not usually cause an allergic reaction or a similar unfavorable reaction, such as stomach disorders, dizziness and the like, when administered to a human or animal. The expression "pharmaceutically acceptable" means that it is approved by a state or federal government regulatory agency or is included in the United States pharmacopeia or in another generally recognized pharmacopeia for use in animals, and particularly in humans.

The term "solvate" refers to any form of the compound according to the invention that has another molecule (most likely a polar solvent) bound thereto by means of a non-covalent bond. Examples of solvates include hydrates and alcoholates, for example methanolate. The solvates are preferably pharmaceutically acceptable solvates.

The salts and solvates can be prepared by means of methods known in the art. For example, the salts of the compounds provided herein can be prepared from the original compound by means of conventional chemical methods, for example, by reacting the free form of these compounds with the suitable base or acid in water or in an organic solvent or in a mixture of both. Examples of acid addition salts include mineral acid addition salts such as, for example, hydrochloride, hydrobromide, hydroiodide, sulfate, nitrate, phosphate salts and organic acid addition salts such as, for example, mono- and di-acetate, maleate, fumarate, citrate, oxalate, succinate, tartrate, malate, mandelate, methanesulfonate and p-toluenesulfonate salts. Examples of alkali addition salts include inorganic salts such as, for example, sodium, potassium, calcium, ammonium, magnesium, aluminum and lithium salts, and organic alkaline salts such as, for example, ethylenediamine, ethanolamine, N,N-dialkylenethanolamine, triethanolamine and basic amino acid salts.

The compounds of the present invention represented by formula (I) described above can include enantiomers depending on the presence of chiral centers or geometric isomers depending on the presence of multiple bonds (for example Z, E). The geometric isomers, enantiomers or diastereoisomers of the compounds of formula (I) and mixtures thereof are within the scope of the present invention.

Compounds of Formula (I)

One aspect of the invention relates to the use of a compound of formula (I) as defined above, or a salt or a solvate thereof, in the preparation of a medicinal product.

According to a particular embodiment, n is 0.

According to a particular embodiment, n is 1 and X represents —C(O)—.

According to a particular embodiment, $R_4$, $R_5$ and $R_7$ are independently selected from the group consisting of H, halogen, OH, optionally substituted $C_1$-$C_3$ alkyl, optionally substituted $C_1$-$C_3$ alkoxy, haloalkyl, $NH_2$, $NO_2$ and CN. In a particular embodiment, $R_4$, $R_5$ and $R_7$ are independently selected from the group consisting of H, halogen, OH, methyl, methoxy, $CF_3$, $NH_2$, $NO_2$ and CN.

According to a particular embodiment, at least one of $R_4$, $R_5$ and $R_7$ is H. In a particular embodiment, at least two of $R_4$, $R_5$ and $R_7$ are H. In a particular embodiment, $R_4$, $R_5$ and $R_7$ are H.

According to a particular embodiment, $R_7$ is H.

According to a particular embodiment, $R_1$ and $R_2$ are independently selected from the group consisting of H, Cl, $NO_2$ and $CF_3$.

According to a particular embodiment, at least one, preferably one, of $R_1$ and $R_2$ is $NO_2$ or halogen, preferably $NO_2$ or Cl.

According to a particular embodiment, one of $R_1$ and $R_2$ is $NO_2$ or halogen, preferably $NO_2$ or Cl, and the other one is H or halogen, preferably H or Cl.

In a particular embodiment, $R_1$ is $NO_2$.

In a particular embodiment, $R_2$ is H or halogen, preferably H or Cl.

According to a particular embodiment, $R_3$ and $R_6$ are independently selected from the group consisting of halogen, OH, optionally substituted $C_1$-$C_3$ alkyl, optionally substituted $C_1$-$C_3$ alkoxy, haloalkyl, $NH_2$, $NO_2$ and CN. In a particular embodiment, $R_3$ and $R_6$ are independently selected from the group consisting of halogen, OH, methyl, methoxy, $CF_3$, $NH_2$, $NO_2$ and CN. In a particular embodiment, $R_3$ and $R_6$ are independently selected from the group consisting of F, Cl, OH, methyl, methoxy, $CF_3$, $NH_2$, $NO_2$ and ON; preferably F, Cl, OH, methyl and methoxy.

According to a particular embodiment, the compound of formula (I) is a compound of formula (Ia):

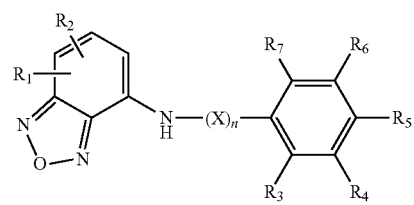

(Ia)

where n, X, $R_1$-$R_7$, and their particular embodiments are as defined above, or a salt or solvate thereof. According to a particular embodiment, $R_1$ is selected from the group consisting of halogen, $NO_2$ and $CF_3$. In a particular embodiment, $R_2$ is H.

In a particular embodiment, the compound of formula (Ia) is a compound of formula (Ia'):

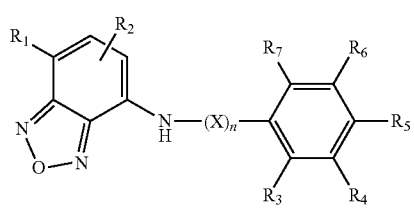

(Ia')

where n, X, $R_1$-$R_7$, and their particular embodiments are as defined above, or a salt or solvate thereof. In a particular embodiment, n is 0. According to a particular embodiment, $R_1$ is selected from the group consisting of halogen, $NO_2$ and $CF_3$. In a particular embodiment, $R_2$ is H.

In another particular embodiment, the compound of formula (I) is a compound of formula (Ib):

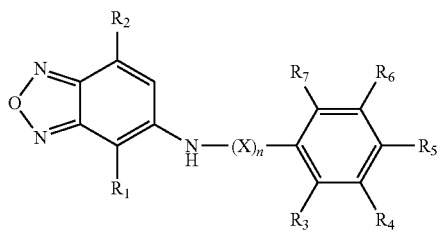

(Ib)

where n, X, $R_1$-$R_7$, and their particular embodiments are as defined above, or a salt or solvate thereof. In a particular embodiment, n is 0. According to a particular embodiment, $R_1$ is selected from the group consisting of $NO_2$ and $CF_3$. In a particular embodiment, $R_2$ is H or halogen, preferably Cl.

According to a particular embodiment, the compound of formula (I) is selected from the group consisting of:

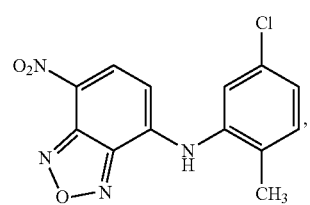

Compound 1

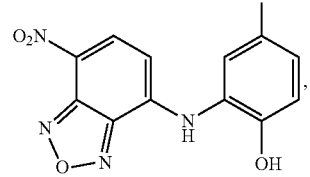

Compound 2

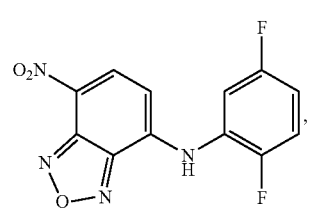

Compound 3

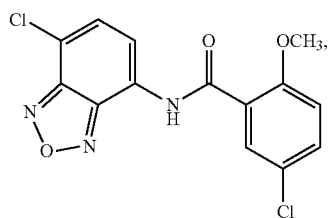

Compound 4

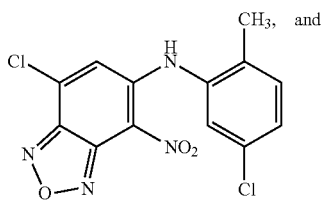

Compound 5

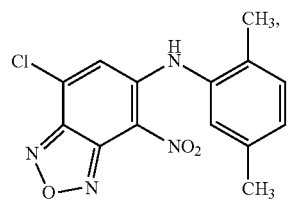

Compound 6 or a salt or solvate thereof.

The compounds of the invention are inhibitors of the activation or the biological activity of p38 MAPK, i.e., they are compounds inhibiting the biological activity of p38 MAPK.

Surprisingly, the capacity of the compounds of the invention, i.e., compounds with a benzo[1,2,5]oxadiazolyl phenyl amine structure which are substituted at least in positions 2 and 5 of the phenyl ring, for inhibiting the activation of p38 MAPK is considerably greater than that of compounds that are structurally related but have a different substitution pattern in the phenyl ring.

Figure 6A:
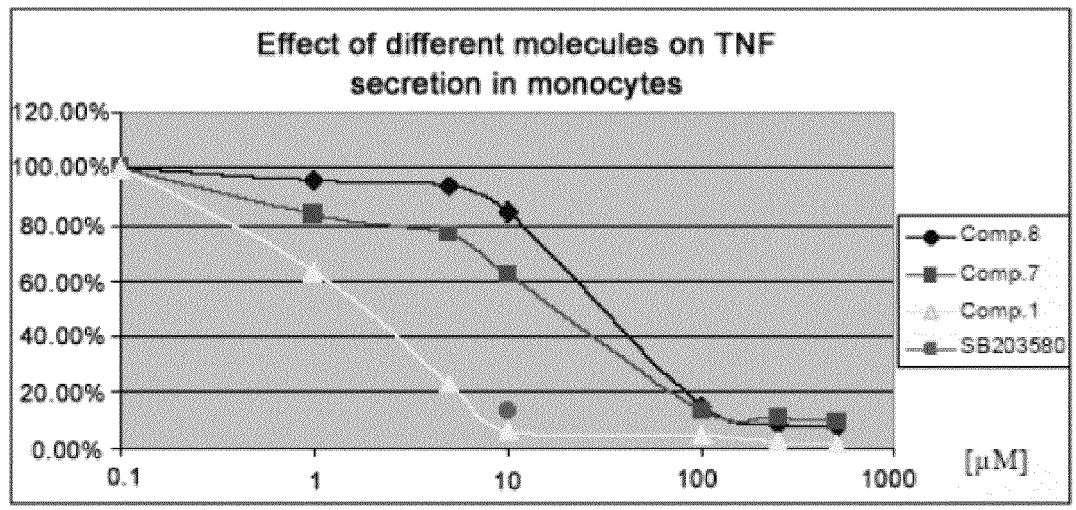
FIG. 6A shows the effect of Compounds 1, 7 and 8 on tumor necrosis factor alpha (TNF-α) secretion in response to bacterial lipopolysaccharide (LPS). Human THP-1 monocytes were preincubated with Compound 1, 7 or 8 dissolved in DMSO at the concentrations indicated on the x-axis and then stimulated with bacterial LPS for 3 hours. The amount of TNF-α secreted into the medium in response to LPS was quantified by means of human TNF ELISA. The results refer to 100% of the control with DMSO.
Figure 6B:
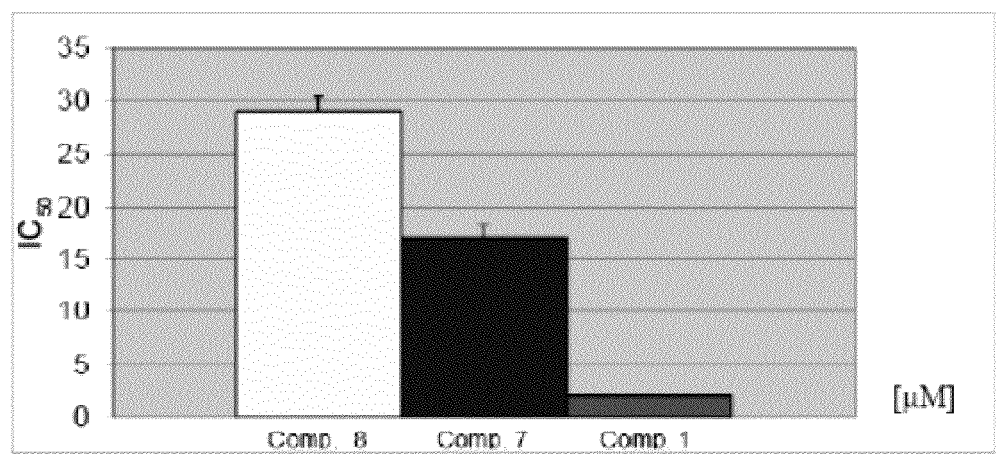
FIG. 6B is a graph showing the mean inhibition ($IC_{50}$) quantification of TNF-α secretion in response to LPS.
Figure 6B:
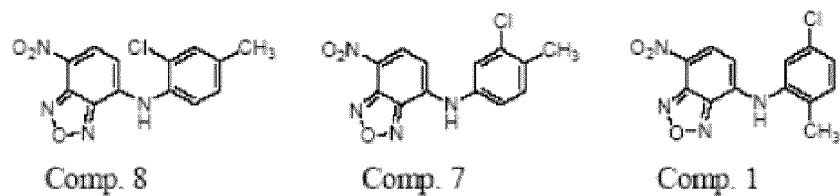

Particularly, comparative Compounds 7 and 8 (see Example 8) only differ from Compound 1 of the invention in the position of the chlorine and methyl substituents in the phenyl ring. As shown in FIG. 6, the capacity of Compound 1, which has substituents in positions 2 and 5 of the phenyl ring, for reducing TNF-α secretion in human THP-1 monocytes stimulated by bacterial LPS is much greater (between 10 and 15 times more powerful) than that of comparative Compounds 7 and 8, which have the same substituents but in different positions of the phenyl ring.

Similarly, comparative Compound 9 (see Example 8 and FIG. 7) described in the document of the state of the art US 2005/0282818, has a lower capacity for reducing TNF-α secretion in human monocytes than that of Compound 3 of the invention, where the substituents of the phenyl ring are in positions 2 and 5.

Figure 8:
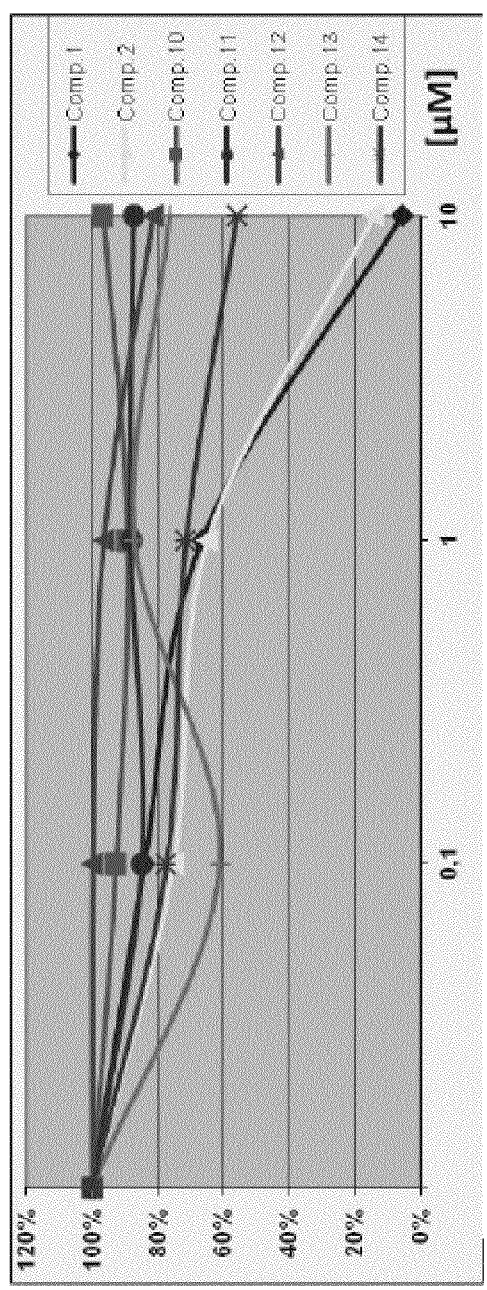
FIG. 8 shows the effect of Compounds 1, 2 and 10-14 on tumor necrosis factor alpha (TNF-α) secretion in response to bacterial lipopolysaccharide (LPS). Human THP-1 monocytes were stimulated with bacterial LPS in the presence of tested compounds dissolved in DMSO at the concentrations indicated on the x-axis. The amount of TNF-α secreted into the medium in response to LPS was quantified by means of an ELISA assay. These comparative results in TNF-α secretion inhibition assays in human monocytes demonstrate that the compounds of the invention (Compounds 1 and 2) have greater activity compared to other compounds that are structurally related but have a different substitution pattern in the phenyl ring (comparative Compounds 10-14).
Figure 8:
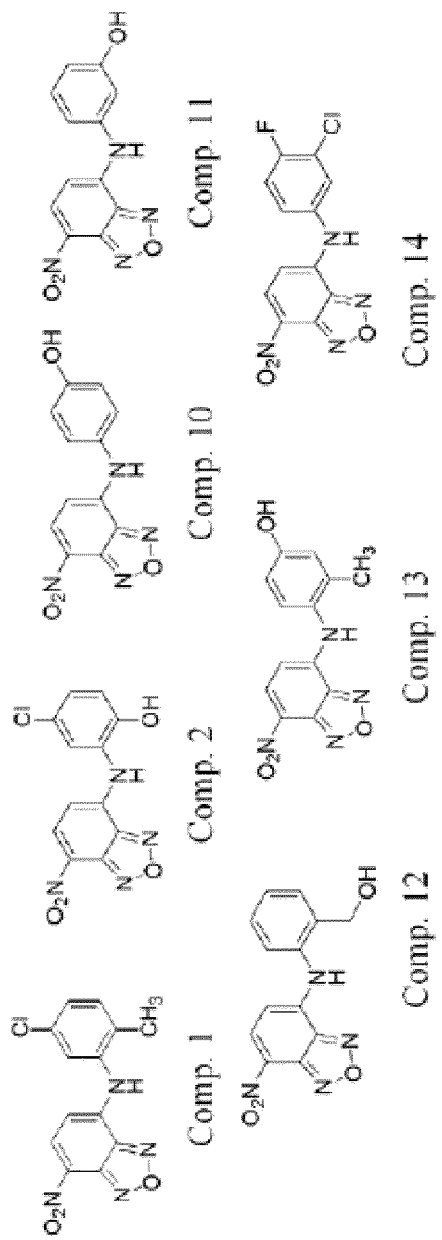

FIG. 8 shows additional comparative results in TNF-α secretion inhibition assays in human monocytes demonstrating greater activity of the compounds of the invention (Compounds 1 and 2) compared to other compounds that are structurally related but have a different substitution pattern in the phenyl ring (comparative Compounds 10-14).

The compounds of the invention can therefore be used in the prevention and/or treatment of a p38 MAPK-regulated disease, such as a disease that can be alleviated by means of inhibiting the activation or the biological activity of said p38 MAPK.

In another aspect, the invention relates to a compound of formula (I) as defined above, with the proviso that the compound of formula (I) is not (5-chloro-2-methyl-phenyl)-(7-chloro-4-nitro-benzo[1,2,5]oxadiazol-5-yl)-amine or (7-chloro-4-nitro-benzo[1,2,5]oxadiazol-5-yl)-(2,5-dimethyl-phenyl)-amine.

In a particular embodiment, said compound of formula (I) is a compound of formula (Ia) as defined above, or a salt or a solvate thereof. In one embodiment, the compound of formula (Ia) is a compound of formula (Ia').

In a particular embodiment, $R_1$ is $NO_2$, halogen, $CF_3$ or CN; preferably $NO_2$ or halogen, more preferably $NO_2$ or Cl, even more preferably $NO_2$.

In a particular embodiment, $R_2$ is H.

Synthesis of the Compounds of Formula (I)

The compounds of the invention can be obtained by conventional synthesis methods. In one aspect, the invention relates to a method for preparing a compound of formula (I), or a salt or solvate thereof.

In a particular embodiment, the compound of formula (I) can be obtained by means of reacting a compound of formula (II)

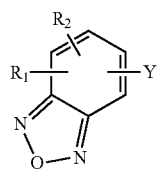

(II)

where Y is halogen, preferably Cl, and $R_1$-$R_2$ are as defined above,
with a compound of formula (III)

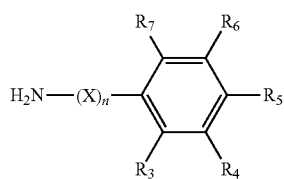

(III)

where n, X and $R_3$-$R_7$ are as defined above.

According to a particular embodiment, the method is carried out in the presence of an organic solvent, such as, for example, a cyclic or acyclic ether (e.g. $Et_2O$, $iPr_2O$, dioxane, tetrahydrofuran, methyltetrahydrofuran), a halogenated solvent (e.g. dichloromethane), an amide (e.g. dimethylformamide), an ester (e.g. EtOAc), a nitrile (e.g. acetonitrile) or mixtures thereof. The reaction is preferably carried out in the presence of ethyl acetate or dimethylformamide.

In a particular embodiment, the reaction is carried out at a temperature between 30° C. and the solvent boiling temperature; preferably at the solvent boiling temperature.

In another particular embodiment, the compounds of formula (I) where n is 1 and X is —C(O)— can also be obtained by means of reacting a compound of formula (IV)

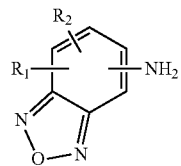

(IV)

where $R_1$-$R_2$ are as defined above,
with a compound of formula (V)

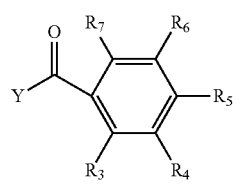

(V)

where Y is halogen, preferably Cl, and $R_3$-$R_7$ are as defined above.

According to a particular embodiment, the method is carried out in the presence of an organic solvent, such as, for example, a cyclic or acyclic ether (e.g. $Et_2O$, $iPr_2O$, dioxane, tetrahydrofuran, methyltetrahydrofuran), a halogenated solvent (e.g. dichloromethane) or mixtures thereof. The reaction is preferably carried out in the presence of tetrahydrofuran.

In a particular embodiment, the reaction is carried out at a temperature between 0 and −80° C.; preferably at −78° C.

Applications of the Compounds of the Invention

The compounds of the invention are powerful p38 MAPK inhibitors. Various assays performed by the inventors have clearly shown that these compounds not only reduce the activation and activity on substrates of said p38 MAPK as well as the secretion of inflammatory cytokines, but they also reduce hyperalgesia in an animal model. The compounds of the invention can therefore be used in the treatment of a p38 MAPK-regulated disease, such as a disease that can be alleviated by means of inhibiting the activation or the biological activity of said p38 MAPK.

In the context of the present invention, the expression "p38 MAPK-regulated disease" or "disease that can be alleviated by means of inhibiting the activation or the biological activity of p38 MAPK" includes any type of diseases presenting with inflammation, for example, inflammatory diseases including autoimmune diseases; heart diseases; cancer; neurodegenerative diseases; metabolic diseases including diabetes and obesity; and diseases presenting with pain [for a recent review, see Coulthard L. R., White D. E., Jones D. L., McDermott M. F., Burchill S. A. Trends Mol. Med. 2009 August; 15(8):369-79]. Said expression preferably refers to diseases presenting with inflammation and/or pain and more preferably to neurodegenerative diseases presenting with inflammation and/or pain.

Multiple sclerosis (MS) is considered a "p38 MAPK-regulated disease" or a "disease that can be alleviated by means of inhibiting the activation or the biological activity of p38 MAPK" since it is a disease presenting with inflammation; it is also considered an autoimmune and neurodegenerative disease.

Amyotrophic lateral sclerosis (ALS) is considered a "p38 MAPK-regulated disease" or a "disease that can be alleviated by means of inhibiting the activation or the biological activity of p38 MAPK" since it is a neuromuscular-type neurodegenerative disease occurring with neuroinflammation, among other factors.

Therefore in a particular embodiment, the invention relates to the use of a compound of formula (I), or a salt or solvate thereof, in the preparation of a medicinal product for the prevention and/or treatment of an inflammatory disease, including autoimmune diseases; a heart disease; cancer; a neurodegenerative disease, preferably a neurodegenerative disease presenting with local neuroinflammation; a metabolic disease, for example, diabetes and obesity; and preferably an inflammatory disease presenting with pain and/or local neuroinflammation.

According to another aspect, the invention relates to a compound of formula (I), or a salt or solvate thereof, for use in medicine. The invention preferably relates to a compound of formula (I), or a salt or solvate thereof, for use in the prevention and/or treatment of an inflammatory disease, including autoimmune diseases; a heart disease; cancer; a neurodegenerative disease, preferably a neurodegenerative disease presenting with local neuroinflammation; a metabolic disease, for example, diabetes and obesity; and preferably an inflammatory disease presenting with pain and/or local neuroinflammation.

In the sense used herein, the expression "inflammatory diseases" includes any disease caused by uncontrolled and continuous activation of inflammatory responses causing tissue damage; said inflammatory response can be triggered by infectious agents, physical agents, chemical agents, tumors and cell death. Autoimmune diseases, insofar as they also have an inflammatory component, fall within the term "inflammatory diseases" as it is used herein, MS for example. Inflammatory diseases are generally classified according to the damaged tissue, for example, (i) inflammatory bowel diseases comprising a group of diseases the main characteristic of which is the presence of chronic, sustained or recurrent bowel inflammation, such as Crohn's disease, ulcerative colitis, microscopic colitis (encompassing collagenous colitis and lymphocytic colitis), eosinophilic enterocolitis, graft-versus-host (GVH) disease and actinic colitis, among others; (ii) inflammatory diseases of the joints, for example, rheumatoid arthritis, gouty arthritis, polymyalgia rheumatica, tendonitis and bursitis, among others; (iii) other inflammatory diseases such as psoriasis and asthma; and (iv) diseases presenting with an inflammatory component even though their etiology is not fundamentally inflammatory.

In a preferred embodiment, the invention relates to the use of a compound of formula (I), or a salt or solvate thereof, in the preparation of a medicinal product for the prevention and/or treatment of a neurodegenerative disease. In a preferred embodiment, the neurodegenerative disease is multiple sclerosis or amyotrophic lateral sclerosis.

As it is used herein, the term "pain" refers to a generally unpleasant (objective) sensory experience and (subjective) emotional experience all living beings having a nervous system can go through. It is an experience associated with tissue injury and can be referred to as acute pain or chronic pain. Acute pain is caused by immediate tissue damage (for example, a burn or a cut). It is a natural defense mechanism in response to tissue damage, preventing the use of the damaged body part and the removal of the painful stimulus. In contrast, chronic pain persists for three months or more and can lead to significant changes in the quality of life of a patient even after the damage has healed [Foley, Pain, Cecil Textbook of Medicine 100-107, J. C. Bennett and F. Plum eds., $20^{th}$ ed., Goldman Bennet 1996]. The compounds of the invention can also be used for the treatment and/or prevention of inflammatory pain generally resulting from an inflammatory response to tissue damage, such as pinched nerves, surgical procedures, cancer or arthritis [Brower, Nature Biotechnology 2000; 18: 387-391]. Most patients with inflammatory pain do not experience continuous pain, but rather experience more pain when they move the inflamed site. In a particular embodiment, the compounds of the invention are used for the treatment and/or prevention of one of the following pain-related disorders: chronic pain, neuropathic pain, toothache, postoperative pain, rheumatoid pain, osteoarthritic pain, backache, visceral pain, pain due to cancer, neuralgia, migraine, neuropathies, diabetic neuropathy-related pain, sciatic neuropathy-related pain, HIV-related neuropathy, postherpetic neuralgia, fibromyalgia, pain associated with nerve fiber damage, pain associated with ischemia, pain associated with neurodegeneration, pain associated with heart attack, post-heart attack pain, pain associated with multiple sclerosis, pain associated with inflammatory disorders, pain associated with inflammatory bowel disease, pain associated with cystitis, pain associated with burns, pain associated with psoriasis. The compounds of the invention are preferably used for the treatment and/or prevention of the following pain-related disorders: neuropathic pain, pain associated with neurodegeneration and pain associated with multiple sclerosis.

As it used in the context of this specification, the term "treatment" means the administration of a compound of the invention for alleviating or eliminating one of the aforementioned diseases or reducing or eliminating one or more symptoms associated with said disease. The term "treatment" also covers alleviating or eliminating the physiological sequelae of the disease. As it is used herein, the term "prevention" refers to the capacity of a compound of the invention for preventing, minimizing or complicating the onset or the development of a disease or condition before the onset thereof.

The compounds of the present invention can be used with at least another drug other than said compound of the invention to provide combined therapy. The at least another drug can be part of the composition or can be provided as a separate composition to be administered at the same time or at a different time. According to a particular embodiment, the at least another drug is an anti-inflammatory or analgesic compound. Virtually any anti-inflammatory or analgesic compound can be used in combination with the compound of the invention. Illustrative, non-limiting examples of said anti-inflammatory compounds which can be used together with the compound of the invention include, though are not limited to, non-steroidal anti-inflammatories, for example, aminoarylcarboxylic acid derivatives (e.g. flufenamic acid, niflumic acid, etc.), arylacetic acid derivatives (e.g. diclofenac, indomethacin, oxamethacin, etc.), arylbutyric acid derivatives (e.g. butibufen, etc.), arylcarboxylic acid derivatives (e.g. ketorolac, etc.), arylpropionic acid derivatives (e.g. ibuprofen, ketoprofen, etc.), pyrazoles (e.g. difenamizole, etc.), pyrazolones (e.g. phenylbutazone, etc.), acetylsalicylic acid derivatives (e.g. acetylsalicylic acid, etc.), thiazinecarboxamides (e.g. isoxicam, piroxicam, etc.), others (e.g. celecoxib, infliximab, rofecoxib, etc.); steroidal anti-inflammatories, for example, betamethasone, cortisone, methylprednisolone, etc.); etc. Likewise, illustrative, non-limiting examples of analgesic compounds that can be used together with the compound of the invention include, though are not limited to, acetylsalicylic acid, calcium acetylsalicylate, perisoxal, sodium salicylate, etc. Additional illustrative examples of said anti-inflammatory or analgesic compounds can be found in The Merck Index, $13^{th}$ Edition, in the "Therapeutic Category and Biological Activity Index" section.

Pharmaceutical Composition of the Invention

The compounds of the invention will be formulated in a suitable pharmaceutical composition for administration to a subject. Therefore in another aspect, the invention relates to a pharmaceutical composition, hereinafter "pharmaceutical composition of the invention", comprising a therapeutically effective amount of at least one compound of the invention, or a salt or solvate thereof, together with at least one pharmaceutically acceptable carrier. Said pharmaceutical composition is useful for administration and/or application o a subject.

As it is used herein, the term "subject" refers to a member of a mammal species and includes, but is not limited to, domestic animals, primates and humans; said subject is preferably a male or female human of any age or race.

In the context of the present invention, "therapeutically effective amount" is understood as the amount of the compound of the invention necessary to achieve the desired effect which, in this specific case, is the treatment and/or prevention of a p38 MAPK-regulated disease. The amount of the compound of the invention that can be present in the pharmaceutical composition of the invention can vary within a broad range. The therapeutically effective amount to be administered will generally depend, among other factors, on the subject to be treated, his/her age, his/her condition, the severity of the disease that said subject suffers, the chosen dosage form, the administration route and frequency, etc. For this reason, the doses that will be administered will be adjusted by a person skilled in the art according to the circumstances.

As it is used herein, the term "pharmaceutically acceptable carrier" refers to a carrier that must be approved by a state or federal government regulatory agency or be listed in the United States pharmacopeia or in another generally recognized pharmacopeia for use in animals and more specifically in humans. The term "carrier" refers to a diluent, coadjuvant, excipient or vehicle with which the compounds of the invention must be administered; said carrier must obviously be compatible with said compounds of the invention. Suitable pharmaceutical carriers are described in "Remington's Pharmaceutical Sciences" by E. W. Martin, 1995.

Examples of pharmaceutical compositions include any solid composition (tablets, pills, capsules, granules, etc.) or liquid composition (solutions, suspensions or emulsions) for oral, topical or parenteral administration.

For the treatment of pathologies for which the compositions are indicated, the active ingredient (compound of the invention) contained in the pharmaceutical composition of the invention can be administered by any means causing said compound of the invention to contact the site of action thereof in the human or animal body. Therefore, the pharmaceutical compositions of the invention can be administered through any suitable administration route, for example, oral route, parenteral route (e.g. subcutaneous route, intramuscular route, intraperitoneal route, intrathecal route, intravenous route, etc.), rectal route, topical route, etc., for which purpose the pharmaceutically acceptable carriers necessary for formulating the desired dosage form will be included. Illustrative, non-limiting examples of oral pharmaceutical dosage forms include tablets, capsules, granulates, solutions, suspensions, etc., which can contain suitable conventional carriers such as binders, diluents, disintegrating agents, lubricants, wetting agents, etc., and can be prepared by conventional methods known by the persons skilled in the art. The pharmaceutical compositions of the invention can also be adapted for parenteral administration in the form of, for example, sterile solutions, suspensions or lyophilized products, in suitable dosage form; in this case, said pharmaceutical compositions of the invention will include suitable pharmaceutically acceptable carriers, such as buffers, surface active agents, etc., and can be prepared by conventional methods known by the persons skilled in the art. Other dosage forms of the pharmaceutical composition of the invention include aerosols, eye drops, ointments, etc., for which suitable pharmaceutically acceptable carriers will be used. In any case, the pharmaceutically acceptable carriers will be chosen depending on the selected pharmaceutical dosage form. A review of the different pharmaceutical dosage forms of drugs and of pharmaceutically acceptable carriers necessary for obtaining same as well as the production methods thereof can be found, for example, in "Tratado de Farmacia Galénica", C. Fauli i Trillo, 1993, Luzán 5, S. A. Ediciones, Madrid; and in Remington's Pharmaceutical Sciences (A. R. Gennaro, Ed.), 20$^{th}$ edition, Williams & Wilkins PA, USA (2000).

The pharmaceutical composition of the invention can contain combinations of two or more compounds of formula (I), or salts or solvates thereof.

The pharmaceutical composition of the invention can contain at least one compound of the invention together with, optionally, at least another drug other than said compound of the invention. According to a particular embodiment, the at least another drug is an anti-inflammatory or analgesic compound. Virtually any an anti-inflammatory or analgesic compound can be used in combination with the compound of the invention. Illustrative, non-limiting examples of said anti-inflammatory and analgesic compounds are as defined above.

EXAMPLES

Compounds of formula (I) according to the present invention can be prepared following the preparation strategy detailed below in the examples. All the reagents used are commercially available.

Compounds 5 and 6 are commercially available.

Example 1

Synthesis of (5-chloro-2-methyl-phenyl)-(7-nitro-benzo[1,2,5]oxadiazol-4-yl)-amine (Compound 1)

A mixture of 4-chloro-7-nitro-2,1,3-benzofurazan (NBD-Cl; 407 mg, 2 mmol) and 5-chloro-2-methylaniline (578 mg, 4 mmol) in ethyl acetate (25 mL) as a solvent in inert atmosphere ($N_2$) was magnetically stirred while heating at reflux (bath temperature=120° C.) for 24 hours. Once this time has elapsed, a saturated aqueous sodium bicarbonate solution (15 mL) was added and the resulting mixture was then poured into an extraction funnel to perform a liquid-liquid extraction process using ethyl ether as an extraction solvent (3×15 mL). The organic phases were washed with brine (45 mL) and then dried with sodium sulfate, it was decanted and concentrated under vacuum to give a reddish crude extract that was purified by chromatography using silica gel as the stationary phase and dichloromethane as the eluent to give 103 mg of compound (contaminated with chloro methyl aniline) that was purified again by crystallization using methanol-water (1:1) as a solvent to give 31 mg of a red solid.

Example 2

Synthesis of 4-chloro-2-(7-nitro-benzo[1,2,5]oxadiazol-4-ylamino)-phenol (Compound 2)

Compound 2 was obtained following a method similar to that described in Example 1, but by using 2-amino-4-chlorophenol instead of 5-chloro-2-methylaniline.

Example 3

Synthesis of (2,5-difluoro-phenyl)-(7-nitro-benzo[1,2,5]oxadiazol-4-yl)-amine (Compound 3)

Compound 3 was obtained following a method similar to that described in Example 1, but by using 2,5-difluoro-aniline instead of 5-chloro-2-methylaniline, and N,N-dimethylformamide as a reaction solvent instead of ethyl acetate.

Example 4

Synthesis of 5-chloro-N-(7-chloro-benzo[1,2,5]oxadiazol-4-yl)-2-methoxy-benzamide (Compound 4)

This compound was obtained using a method consisting of the three following steps.

Step 1: Reduction of NBD-Cl. A solution of NBD-Cl (200 mg, 1 mmol) in acetic acid (4 mL), ethyl acetate (2 mL) and water (0.4 mL) was heated to 50° C. and then treated with metal iron (280 mg, 50.2 mmol). The resulting mixture was magnetically stirred at 80° C. for 30 minutes and then left to cool to room temperature. The mixture was then filtered through celite, eluting with ethyl acetate. The filtrate was treated with a saturated aqueous sodium bicarbonate solution, dried with magnesium sulfate, decanted and finally concentrated under vacuum to give an orangey-reddish crude solid that was purified by chromatography using silica gel as the stationary phase and dichloromethane as the eluent to give 113 mg of compound (yield=66%).

Step 2: Obtaining acid chloride. Thionyl chloride (0.170 mL, 2.31 mmol) was added to a solution of 5-chloro-2-methoxybenzoic acid (124 mg, 0.66 mmol) in benzene (0.8 mL) in inert atmosphere ($N_2$). The resulting mixture was stirred under reflux in benzene under inert atmosphere for 4 hours. The unreacted benzene and thionyl chloride were then evaporated, giving a colorless oil that was directly subjected to the following step of synthesis.

Step 3: Amidation. A commercial n-butyllithium solution (1.6 molar in hexane) (0.4 mL, 0.61 mmol) was added dropwise to a solution cooled to −78° C. of the aniline obtained in step 1 (102 mg, 0.6 mmol) in tetrahydrofuran (1 mL) under inert atmosphere, a change in color to black after the addition being observed. After 5 minutes, a solution of the acyl chloride obtained in step 2 in tetrahydrofuran (0.5 mL) was added to the solution. The resulting mixture was stirred at −78° C. for 30 minutes and left to heat to room temperature for another 30 minutes. A saturated aqueous ammonium chloride solution (15 mL) was then added to the reaction mixture and the solvent was evaporated under vacuum. The obtained crude was subjected to extraction using dichloromethane as a solvent (2×15 mL), the organic extracts were washed with an aqueous sodium hydroxide solution (1 M) (30 mL), washed again with brine (30 mL), dried with sodium sulfate, decanted, concentrated under vacuum and the obtained crude was purified by chromatography using silica gel as the stationary phase and a mixture of hexane-ethyl acetate (7:3) as the eluent to give 20 mg of compound (yield=10%).

Example 5

Inhibition of MEF-2 Phosphorylation by p38 MAPK

This assay was performed to quantify the effect of the compounds of the invention on MEF2-A phosphorylation by p38 MAPK in vitro.

To that end, briefly, active recombinant p38 (1 nM) and MEF2A (10 nM) were incubated with different concentrations of Compound 1 in a kinase buffer for 5 minutes. The proteins were resolved using SDS-PAGE and the activity of p38 was measured as phosphorylated MEF2A using anti-P-MEF2A (T312), a specific antibody. The mean of the results is graphically depicted as a percentage with respect to the controls (DMSO) of two independent experiments conducted in duplicate. For comparative purposes, Compound 5 at a concentration of 10 µM was used.

Finally, the in vitro mean inhibitory concentration ($IC_{50}$) of this reaction for each assayed compound was determined as the measurement of the efficacy of a compound for inhibiting this biochemical function using a sufficient range of concentrations of each of these compounds (data not shown). The results of the $IC_{50}$ obtained in each case are shown in Table 1 and in FIG. 1.

TABLE 1

| $IC_{50}$ of the assayed compounds | |
|---|---|
| Compound | $IC_{50}$ (µM) |
| Compound 1 | 6.5 |
| Compound 5 | 10 |

Example 6

Inhibition of the Activation of p38 MAPK in Response to LPS and of Its Activity in Human Monocytes This assay was performed to analyze the effect of Compound 1 on the activation of p38 MAPK and on its activity in a human monocytic cell line (THP-1) (American Type Culture Collection: http://www.atcc.org/) treated with different concentrations of said compound.

Briefly, human monocytic cells from said THP-1 cell line at a density of about $10^6$ cells/ml were stimulated with bacterial LPS (Sigma #L2654) at a concentration of between 1 and 10 mg/ml (which may vary depending on the batch) for 1 hour in the absence or presence of Compound 1 at different concentrations (1 µM and 5 µM) dissolved in dimethyl sulfoxide (DMSO). DMSO was used as a control. The cells were lysed in a 100 mM pH 7.5 Tris/HCl buffer, 200 mM EDTA, 1 µM benzamidine, 10 mg/ml STI (soy trypsin inhibitor), 10 mg/ml bacitracin, 80 mU/ml aprotinin, 100 µM phenylmethanesulfonyl fluoride (PMSF) and phosSTOP (Roche, Ref.#04906845001). The samples were subsequently analyzed using Western Blot with specific antibodies. Briefly, the activation of p38 MAPK was analyzed by quantifying by densitometry the amount of p38 MAPK phosphorylated in the activation loop (TGY) by means of Western Blot with anti-phospho-T180-Y182-p38 antibodies (Cell Signaling, Ref.#9211) and by normalizing the values with those obtained for total p38 MAPK levels in each lysate. Likewise, the activity of p38 MAPK was quantified by densitometry of the phosphorylation of its MK2 and Hsp27 substrates analyzed by means of Western Blot with specific antibodies targeting said phosphorylated proteins: anti-phospho-T334-MK2 (Cell Signaling, Ref.#3041) and anti-phospho-S78-HSP27 (Cell Signaling, Ref#2405) and normalizing the values with those obtained for the total p38 MAPK levels in each lysate.

Figure 2A:
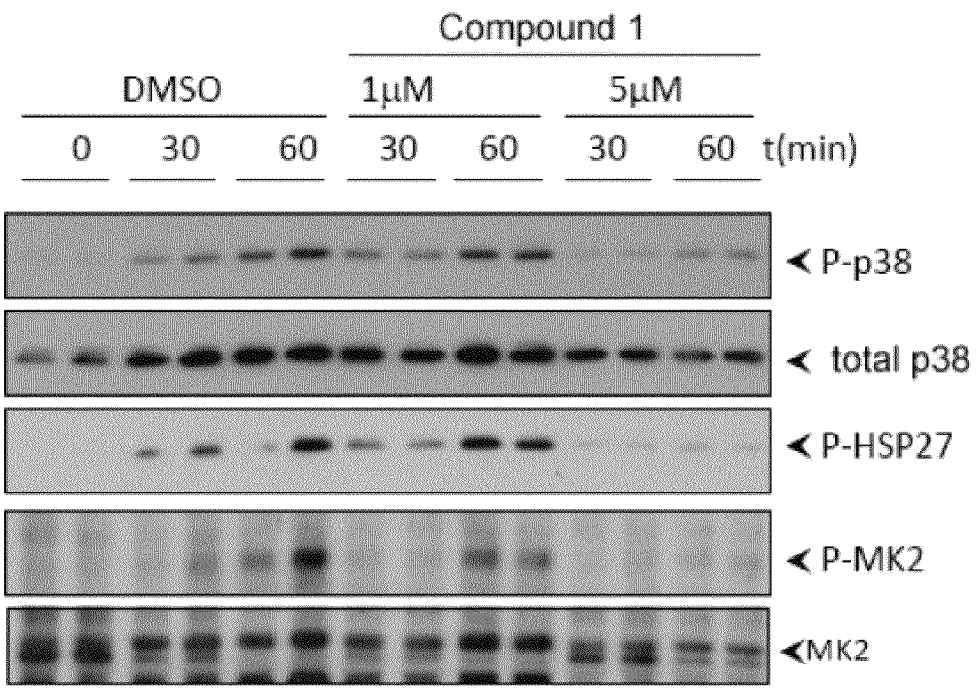
FIG. 2 shows the effect of Compound 1 on the activation of different components of the p38 MAPK, MK2 and Hsp27 pathway in response to LPS in a human monocytic cell line (THP-1). The THP-1 cells were preincubated with the indicated doses of Compound 1 (1 and 5 µM) for 1 hour and stimulated with LPS for 30 or 60 minutes. The cells were lysed and the cell lysates were resolved by means of SDS-PAGE and their proteins were analyzed by Western Blot with specific antibodies (FIG. 2A), and the films were quantified by densitometric analysis. The activation of p38 MAPK, MK2 and Hsp27 was analyzed by quantifying the amount of phosphorylated protein by densitometry and by normalizing the values with those obtained for total protein levels in each lysate (FIG. 2B), and making them proportional to 100%, where the values obtained for the controls with DMSO represent 100%.

The Western Blot results are shown in FIG. 2A, where "P-p38" is p38 MAPK phosphorylated in the activation loop (TGY), "total p38" is total p38 MAPK, "P-MK2" is phosphorylated MK2, and "P-HSP27" is phosphorylated Hsp27.

Figure 2B:
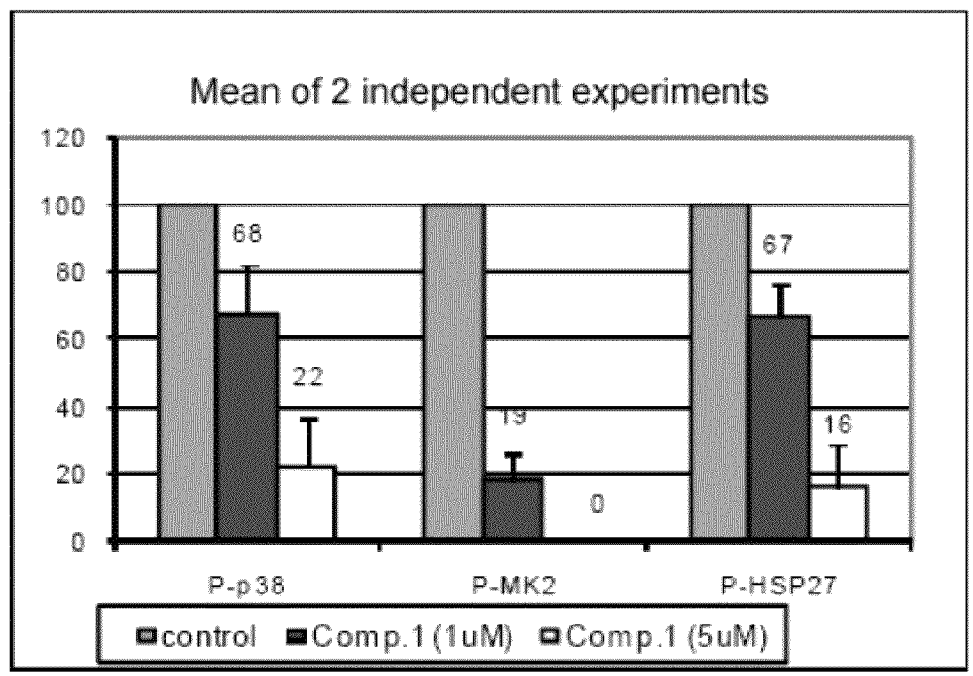

The results obtained in the Western Blot were normalized and related to the value of TNF-α secreted in the absence of compound (DMSO, 100%) and are shown in FIG. 2B, where a decrease in the activation of p38 MAPK in the presence of Compound 1 and, therefore, a decrease in the phosphorylation of MK2 and Hsp27 substrates are shown. The obtained results demonstrate that the presence of Compound 1 is capable of inhibiting both the activation of p38 and the transmission of its signal to its substrates in human monocytic cells, which indicates that said compound is an effective p38 MAPK pathway inhibitor.

Example 7

TNF-α Secretion in Response to LPS and Monocyte Survival in the Presence of p38 MAPK-Inhibiting Compounds This assay was performed to analyze the effect of the compounds of the invention on tumor necrosis factor alpha (TNF-α) secretion in response to bacterial lipopolysaccharide (LPS) in human monocytes (THP-1) and on the survival of said THP-1 monocytes in the presence of said compounds.

Figure 4:
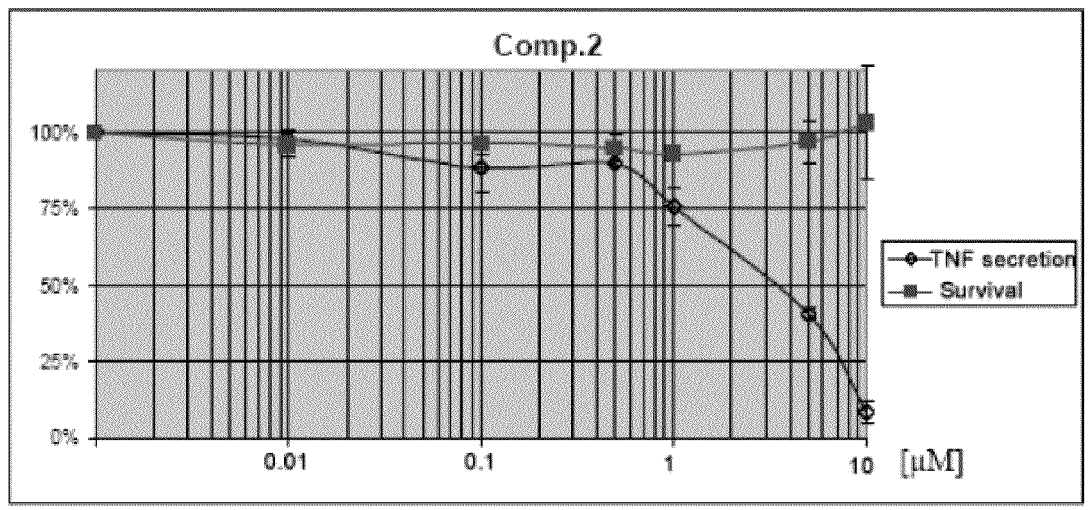
Figure 5:
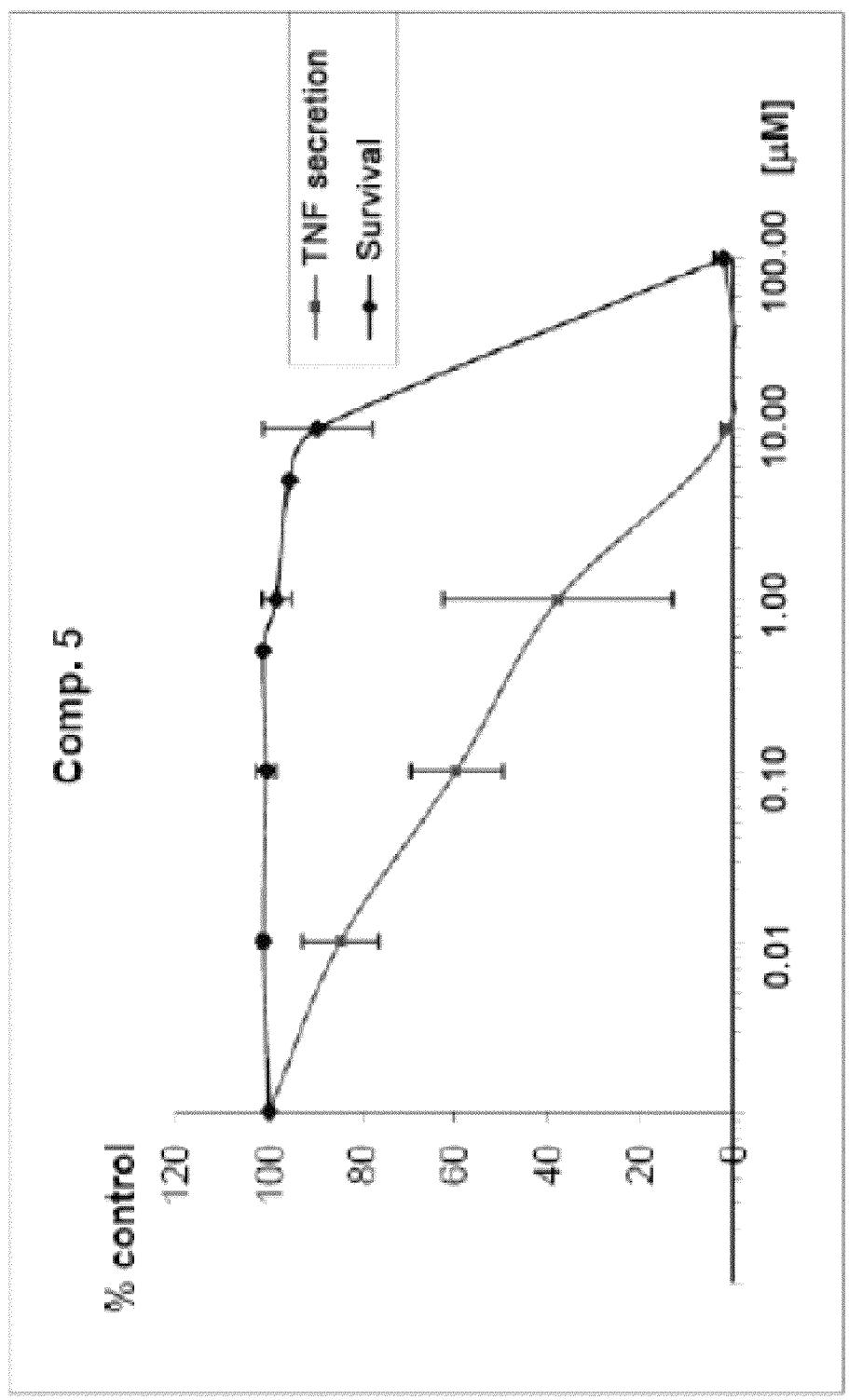

Briefly, cells from human monocytic cell line THP-1 (ATCC) at a density of about $10^6$ cells/ml were stimulated with bacterial LPS (Sigma, Ref.# L2654) at a concentration of 1 mg/ml for 4 hours in the presence of the compounds of the invention dissolved in dimethyl sulfoxide (DMSO) at different concentrations (0.001, 0.01, 0.1, 1, 10 and 100 μM). The amount of TNF-α secreted into the medium in response to LPS was quantified by means of an ELISA assay (BioTrak, Ref.# RPN2758, GE-Amersham) following the manufacturer's instructions. Cell viability was quantified by means of flow cytometry FACS (FACScalibur, Becton Dickinson) after staining the treated cells with propidium iodide (1 mg/l) and quantifying the amount of positive cells for this stain (Software Cell Quest Pro). The results obtained are shown in Table 2 and in FIGS. 3-5.

TABLE 2

$IC_{50}$ and $TD_{50}$ of the assayed compounds

| Compound | $IC_{50}$ (μM) | $TD_{50}$ (μM) |
| --- | --- | --- |
| Compound 1 | 1.8 ± 0.006 μM (n = 3) | ≈200 μM (n = 2) |
| Compound 2 | 3.2 ± 0.25 μM (n = 3) | >100 μM (n = 2) |
| Compound 3 | 2.9 ± 0.41 μM | — |
| Compound 4 | 3.2 μM | — |
| Compound 5 | 0.3 μM (n = 3) | >35 μM (n = 3) |
| Compound 6 | 3 μM | — |

$IC_{50}$: Mean inhibitory concentration [compound concentration causing 50% inhibition of a biological or biochemical function].
$TD_{50}$: Mean toxic dose [compound dose causing the death of 50% of the cells in a sample].
n = number of independent experiments conducted to determine each magnitude.

The results obtained clearly show that the compounds of the invention are capable of reducing TNF-α secretion in human THP-1 monocytes stimulated by bacterial LPS.

Example 8

Comparative Assays of TNF-α Secretion in Response to LPS

These assays were performed to compare the effect of the compounds of the invention (compounds 1, 2 and 3) on tumor necrosis factor alpha (TNF-α) secretion in response to bacterial lipopolysaccharide (LPS) in human monocytes (THP-1) with respect to compounds that are structurally related but have a different substitution pattern in the phenyl ring. Conditions similar to those described in Example 7 were used.

The results obtained in the comparative assay between Compound 1 and the corresponding positional isomers (Compounds 7 and 8) are shown in Table 3 and in FIG. 6.

TABLE 3

$IC_{50}$ of the assayed compounds

| Compound | Structure | $IC_{50}$ (μM) |
| --- | --- | --- |
| Compound 1 | 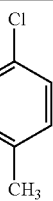 | 1.8 ± 0.01 μM |
| Compound 7 (comparative) | 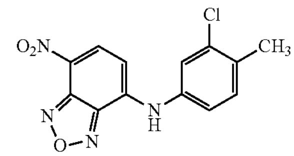 [SMILES: Cc1ccc(Nc2ccc([N+](=O)[O-])c3nonc23)cc1Cl] | 17 ± 1.41 μM |
| Compound 8 (comparative) | 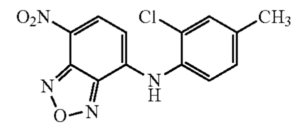 [SMILES: Cc1ccc(Nc2ccc([N+](=O)[O-])c3nonc23)c(Cl)c1] | 29 ± 1.41 μM |

Figure 7:
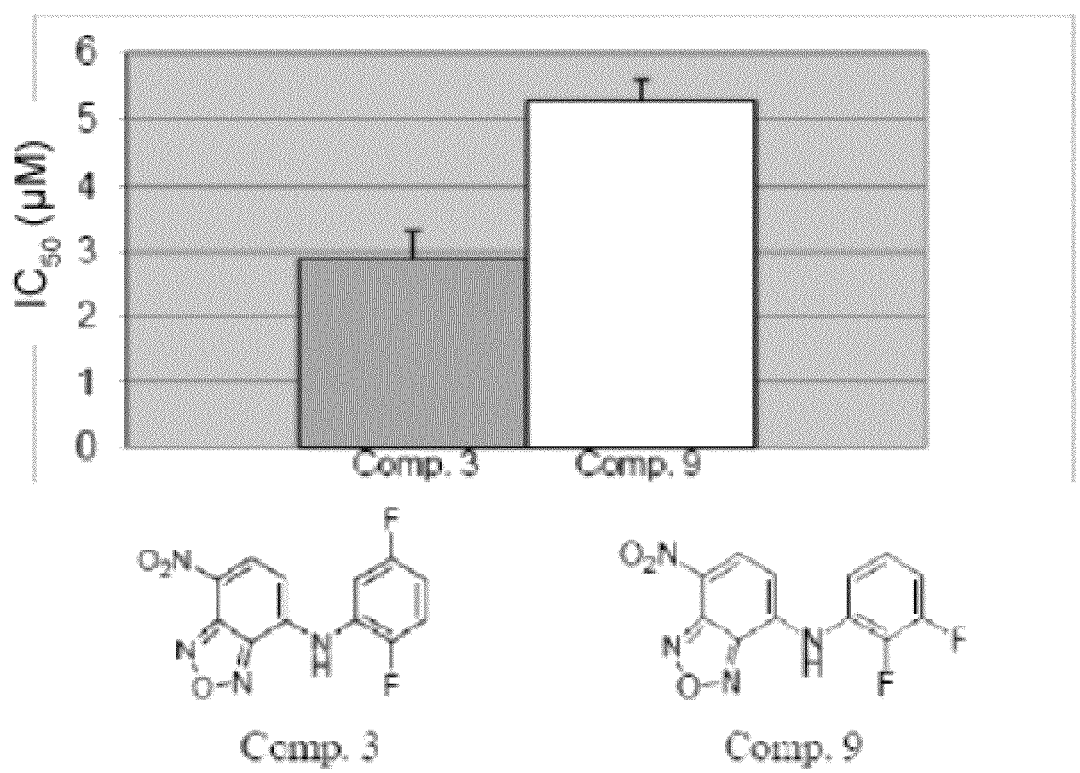
FIG. 7 is a comparative graph showing the mean inhibition ($IC_{50}$) quantification of TNF-α secretion in response to LPS of Compounds 3 and 9 as an indicator of their potency. THP-1 cells were preincubated with the indicated doses of Compound or DMSO for 1 hour and stimulated with LPS for 3 hours. The amount of TNF that was secreted in the cell supernatant was quantified using a human TNF ELISA kit. The results refer to 100% of the control with DMSO.

The results obtained in the comparative assay between Compound 3 and the corresponding positional isomer (Compound 9, described in the document of the state of the art US 2005/0282818) are shown in Table 4 and in FIG. 7.

TABLE 4

$IC_{50}$ of the assayed compounds

| Compound | Structure | $IC_{50}$ (μM) |
| --- | --- | --- |
| Compound 3 | 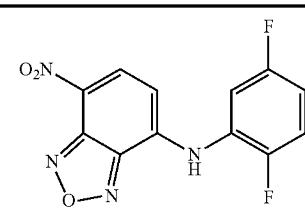 | 2.9 ± 0.41 μM |
| Compound 9 (comparative, US2005/ 0282818) | 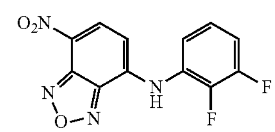 [SMILES: O=[N+]([O-])c1ccc(Nc2cccc(F)c2F)c2nonc12] | 5.25 ± 0.35 μM |

The results obtained in the comparative assay between Compounds 1 and 2 of the invention and other compounds that are structurally related but have a different substitution pattern in the phenyl ring (comparative Compounds 10-14) are shown in FIG. 8.

The obtained results clearly show that capacity of the compounds of the invention, i.e., compounds which are substituted at least in positions 2 and 5 of the phenyl ring, for reducing TNF-α secretion in human THP-1 monocytes stimulated by bacterial LPS is considerably greater than that of compounds that have a different substitution pattern in the phenyl ring, i.e., compounds that are not substituted in positions 2 and 5 of the phenyl ring.

Example 9

Effect of p38 MAPK-Inhibiting Compounds on Hyperalgesia Induced in Mice

This assay was performed to analyze the effect of Compounds 1 and 5 on hyperalgesia induced in mice.

Example 9A

To perform this assay, a previously described protocol was followed [Willemen H L, et al., Microglial/macrophage GRK2 determines duration of peripheral IL-1beta-induced hyperalgesia: contribution of spinal cord CX3CR1, p38 and IL-1 signaling. Pain. 2010 September; 150(3):550-60; and Eijkelkamp N, et al., (http://www.ncbi.nlm.nih.gov/pubmed/20147541; J. Neurosci. 2010 Feb. 10; 30(6):2138-49). Briefly, eight female LysM-GRK2$^{f/+}$ mice (2 mice per group, 4 paws for each condition) were subjected to an intraplantar injection of carrageenan (Sigma-Aldrich, 5 mL of a 1% solution in saline) for inducing inflammatory-type hyperalgesia in the extremities. Seven (7) days after injecting carrageenan, the paw withdrawal latency time when the paw is in contact with heat was determined as an indication of inflammatory-type pain at time 0 (T=0). The carrier (20% DMSO) or Compound 1 at different concentrations (0.15, 0.5 and 1.5 μg in 5 μL of 20% DMSO) was then intrathecally injected.

Figure 9A:
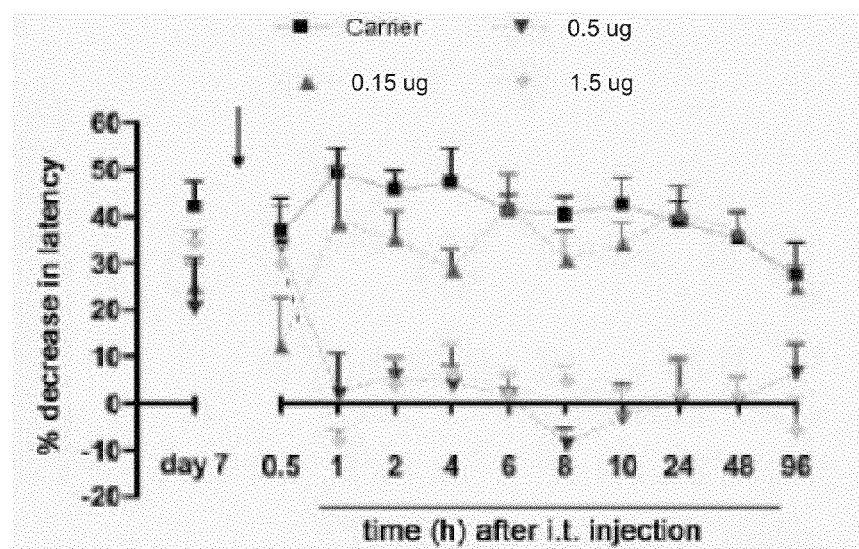
FIGS. 9A and 9B show the effect of Compound 1 on hyperalgesia induced in LysM-GRK2$^{f/+}$ mice by means of intraplantar injection of carrageenan. Seven (7) days (FIG. 9A) or six (6) days (in the FIG. 9B) after inducing hyperalgesia, the paw withdrawal latency time when the paw is in contact with heat was determined as indicative of inflammatory-type pain at time 0. The carrier (DMSO) or Compound 1 at different concentrations was then intrathecally injected, and the paw withdrawal latency periods that are represented on the y-axis were measured at the times indicated on the x-axis. The means±SEM of the percentages of decrease obtained in latency times are plotted in a graph ***, P<0.001.
Figure 9B:
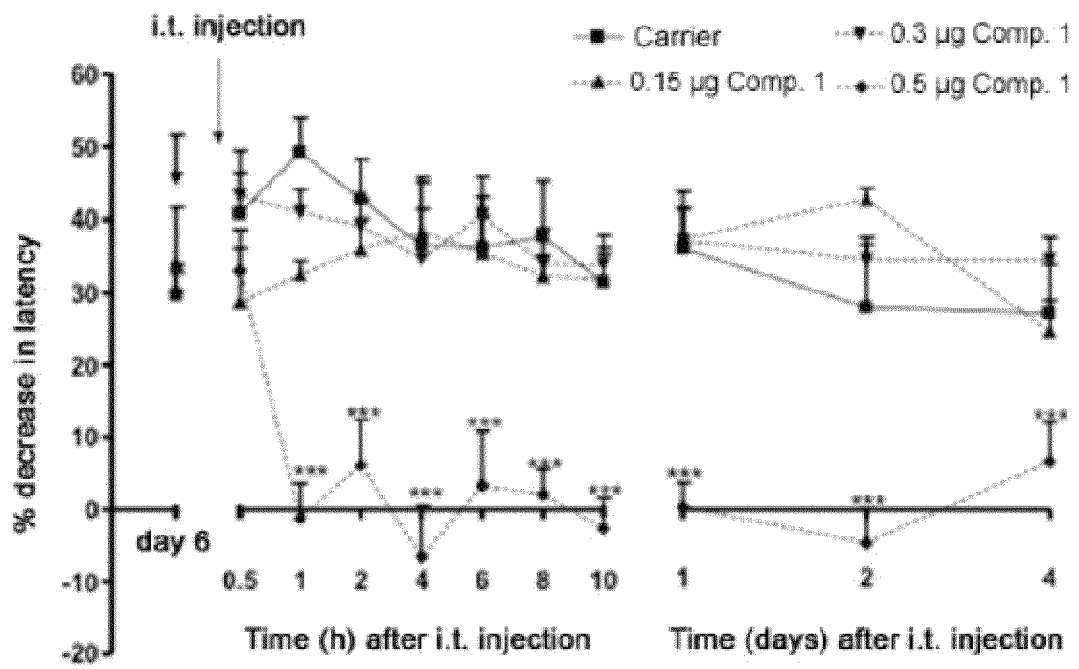

The paw withdrawal latency periods were then measured at different times (0.5, 1, 2, 4, 6, 8, 10, 24, 48 and 96 hours after injecting the compound). The obtained results are shown in FIG. 9A. As can be seen, the administration of Compound 1 at doses of 0.5 and 1.5 μg led to an almost complete reduction of hyperalgesia induced in mice that was maintained at least until 96 hours after administering the compound. The lowest effective dose in this model was established at 0.5 μg of Compound 1, since a dose of 0.3 μg did not provide any long-term analgesic effect (FIG. 9B).

Figure 10:
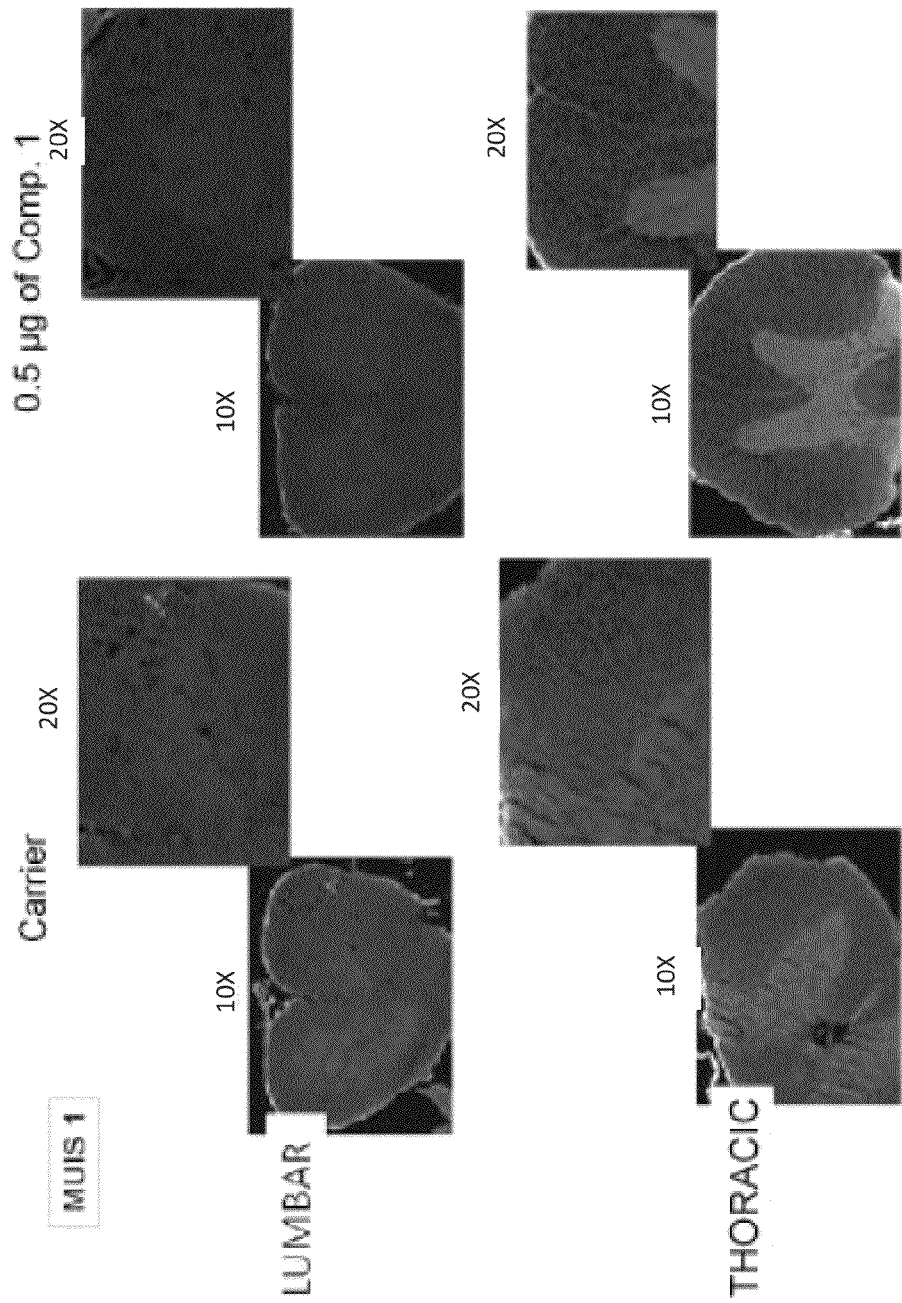
FIG. 10 shows the cells surrounding the injection site (spinal cord astrocytes and neurons) after the intrathecal injection of Compound 1 in LysM-GRK2$^{f/+}$ mice and staining with Fluoro-Jade B. The cells surrounding the injection site (spinal cord astrocytes and neurons) were stained with Fluoro-Jade B two days after the injection to resolve dead or damaged cells after the intrathecal injection of Compound 1 in LysM-GRK2 mice. There are hardly any dead cells (which would be positive for this stain).

Furthermore, the possible toxicity of Compound 1 at the injection site (intrathecal) was measured. As shown in FIG. 10, no signs of neurotoxicity were detected for Compound 1 injected intrathecally in the injection site.

Example 9B

Figure 11A:
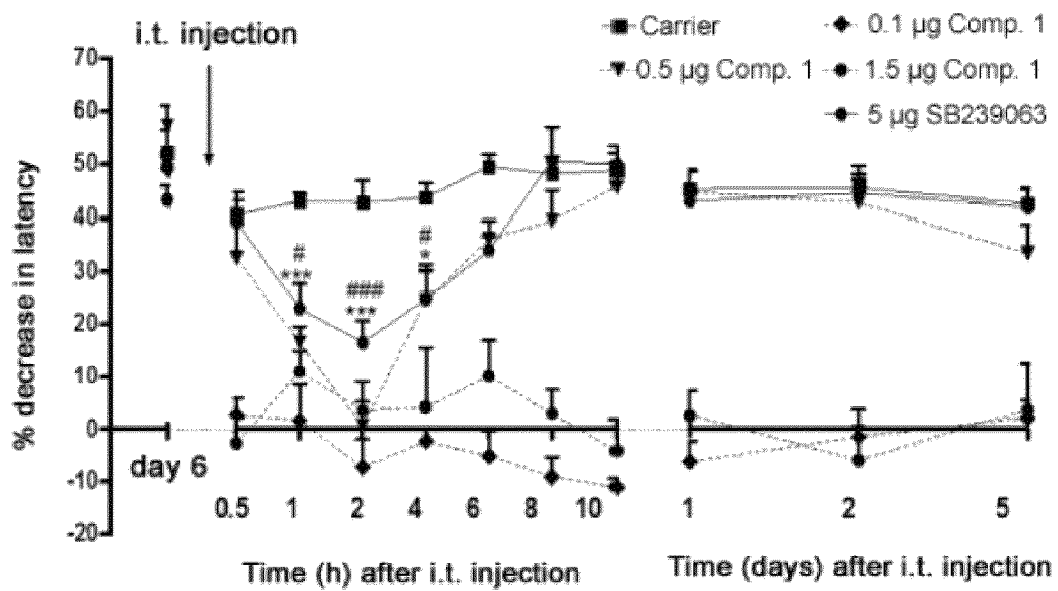
FIGS. 11A and 11B shows the effect of Compound 1 on hyperalgesia induced in C54BL/6 wild-type mice by means of intraplantar injection of high doses of carrageenan. Six (6) days after inducing hyperalgesia, the paw withdrawal latency time when the paw is in contact with heat was determined as indicative of inflammatory-type pain at time 0. The carrier (DMSO), compound SB239063 (a known p38 MAPK inhibitor), or Compound 1 (FIG. 11A) or Compound 13 (FIG. 11B) at different concentrations was then intrathecally injected, and the paw withdrawal latency periods that are represented on the y-axis were measured at the times indicated on the x-axis. Means±SEM of the percentages of decrease obtained in latency times are plotted in a graph. * or # P<0.05; *** or # # # P<0.001. C)
Figure 11B:
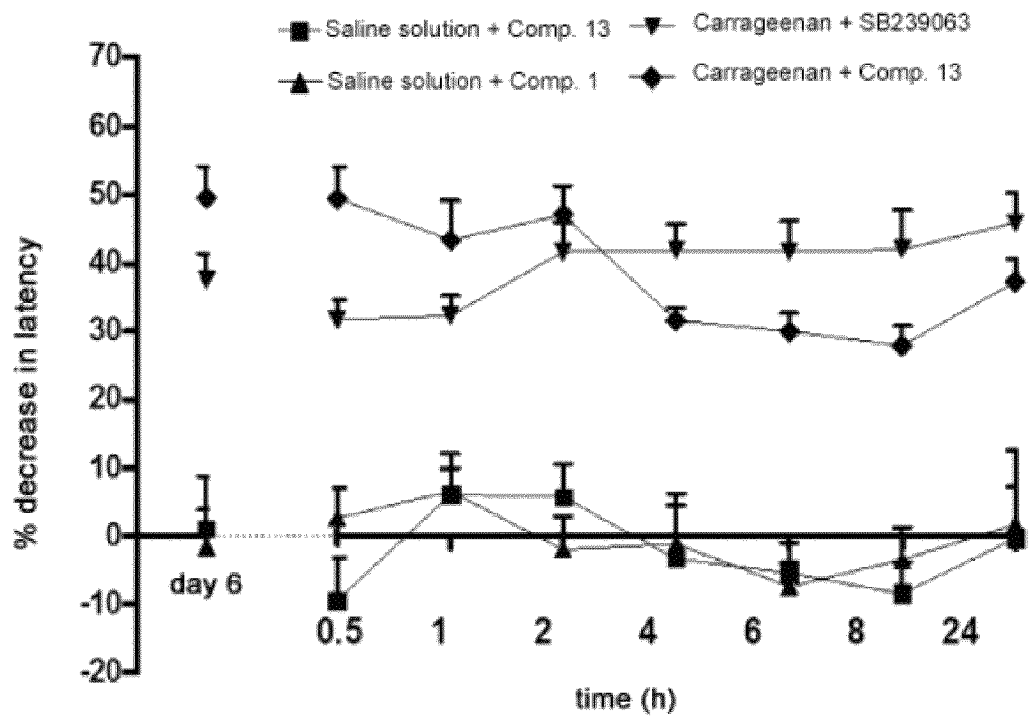

The administration of high doses of carrageenan is known to induce hyperalgesia and prolonged inflammation in wild-type mice. Briefly, 16 female wild-type mice of strain C54BL/6 (4 mice per group, 8 paws for each condition) were subjected to intraplantar injection of carrageenan (Sigma-Aldrich, 20 μL of a 2% solution % in saline) for inducing inflammatory-type hyperalgesia in the extremities. Six (6) days after injecting carrageenan, the paw withdrawal latency time when the paw is in contact with heat was determined as an indication of inflammatory-type pain at time 0 (T=0). The known p38 MAPK inhibitor SB239063 [trans-4-[4-(4-fluorophenyl)-5-(2-methoxy-4-pyrimidinyl)-1H-imidazol-1-yl]cyclohexanol] (5 μg in 5 μL of 20% DMSO), the carrier (20% DMSO), or Compound 1 at different concentrations (0.5, 1.0 and 1.5 μg in 5 μL of 20% DMSO) was then intrathecally injected. The obtained results are shown in FIG. 11A. As can be seen, the administration of Compound 1 produces a long-term analgesic effect in wild-type mice of strain C57BL/6 in response to the induction of inflammatory pain with high doses of carrageenan, producing a temporary effect at a dose of 0.5 μg and a long-term analgesic effect (at least 5 days) at doses of 1 and 1.5 μg. Thermal sensitivity in control mice treated with saline solution was not affected by Compound 1 (FIG. 11B). By way of comparison, Compound 13 did not have an analgesic effect on carrageenan-induced hyperalgesia (FIG. 11B).

To investigate the possible neurotoxicity of Compound 1, the spinal cord was isolated two days after intrathecal treatment with said compound, and the sections were stained with Fluoro-Jade B (FIG. 11C). The presence of positive cells for Fluoro-Jade B was not observed, and the morphology of the spinal cord was not affected by the intrathecal injection of 1 μg of Compound 1, indicating that the beneficial effect of Compound 1 on inflammatory hyperalgesia is not mediated by a neurotoxic effect on the spinal cord.

Figure 3:
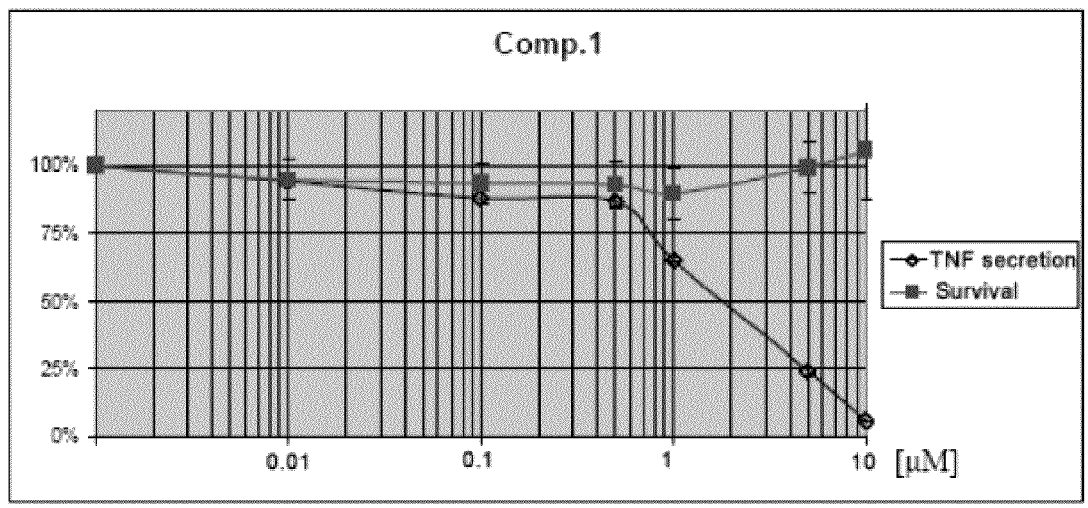
FIGS. 3-5 show the effect of Compounds 1 (FIG. 3), 2 (FIG. 4) and 5 (FIG. 5) on tumor necrosis factor alpha (TNF-α) secretion in response to bacterial lipopolysaccharide (LPS) and survival in THP-1 monocytes. Human THP-1 monocytes were preincubated with Compounds 1, 2 or 5 dissolved in DMSO at the concentrations indicated on the x-axis, or DMSO for 1 hour and then stimulated with bacterial LPS for 3 hours. The amount of TNF-α secreted into the medium in response to LPS was quantified by means of a human TNF ELISA. Cell viability was quantified by means of flow cytometry (FACS) after staining the treated cells with propidium iodide and quantifying the amount of positive cells for that stain. The results are the average of 3 independent experiments, each performed in duplicate, and refer to 100% of the control with DMSO.

Cell culture experiments showed that Compound 1 inhibits LPS-induced TNF-α production (FIG. 3). To find out if TNF-α levels are repressed in vivo after treatment with Compound 1, the spinal cord was isolated two days after intrathecal treatment with said compound and TNF-α levels were analyzed with ELISA. The intraplantar injection of carrageenan causes a significant increase in TNF-α in the spinal cord and subsequent intrathecal treatment with Compound 1 significantly reduces TNF-α levels (FIG. 11D). As can be seen, Compound 1 alone has no effect on TNF-α secretion (FIG. 11D). Six days after treatment with Compound 1, mouse paw thickness increased, which indicates that treatment with Compound 1 does not directly affect peripheral inflammatory activity (FIG. 11E).

Example 9C

Figure 12:
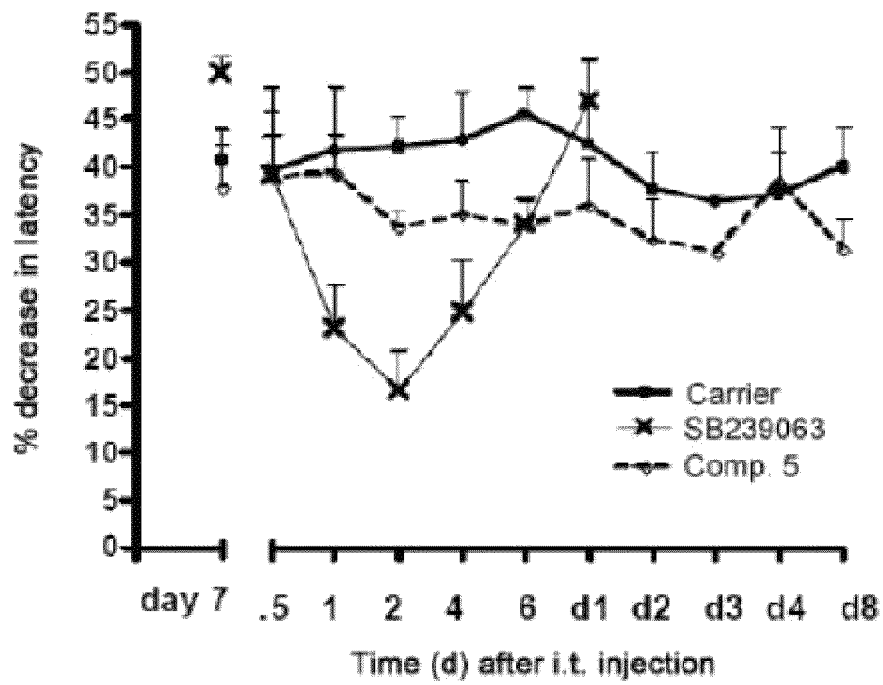
FIG. 12 shows the effect of Compound 5 and Compound SB239063 on hyperalgesia induced in LysM-GRK2$^{f/+}$ mice by means of intraplantar injection of carrageenan, Seven (7) days after inducing hyperalgesia, the paw withdrawal latency time when the paw is in contact with heat was determined as indicative of inflammatory-type pain at time 0. The carrier (DMSO), compound SB239063, or Compound 5 was then intrathecally injected, and the paw withdrawal latency periods that are represented on the y-axis were measured at the times indicated on the x-axis.

To evaluate the effect of Compound 5 on hyperalgesia induced in mice, a protocol similar to that described for Compound 1 in Example 9A was followed, but in this protocol, the known p38 MAPK inhibitor SB239063 (5 μg in 5 μL of 20% DMSO), the carrier (20% DMSO), or Compound 5 (4 μg in 5 μL of 20% DMSO) was intrathecally injected 7 days after injecting the carrageenan. The obtained results are shown in FIG. 12. As can be seen, the administration of Compound 5 caused a decrease in hyperalgesia induced in mice that can be detected 8 days after administering Compound 5, which is a considerable improvement over the effect caused by SB239063.

Example 10

Figure 13:
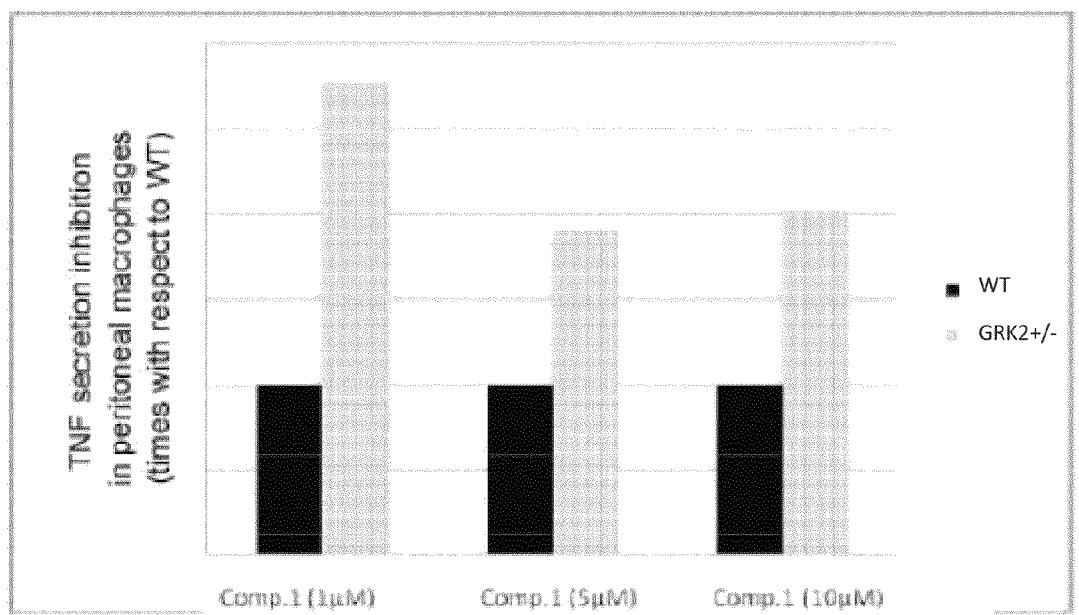
FIG. 13 shows the effect of Compound 1 on TNF-α secretion by peritoneal macrophages of WT and GRK2$^{+/-}$ mice. GRK2$^{+/-}$ peritoneal macrophages were subjected to treatment with LPS and TNF secretion was measured in the presence of increasing doses of Compound 1 as described above. The inhibition observed in GRK2$^{+/-}$ macrophages was greater than that obtained for WT cells for all doses of Compound 1. The data are means of points in duplicate referring in each case to the secretion obtained in WT macrophages in the presence of Compound 1 at the same dose.

Effect of Compound 1 on LPS-Induced TNF-α Secretion in Peritoneal Macrophages of WT and GRK2$^{+/-}$ Mice TNF-α secretion inhibition in peritoneal macrophages of GRK2$^{+/-}$ mice with Compound 1 was studied. As can be observed in FIG. 13, the greater effect of Compound 1 on GRK2$^{+/-}$ macrophages may indicate that cells with a lower GRK2 level, as occurs in immune system cells from patients with inflammatory pathologies (Vroon A, Kavelaars A, Limmroth V, Lombardi M S, Goebel M U, Van Dam A M, Caron M G, Schedlowski M, Heijnen C J., *J Immunol.*, 2005, 174(7), 4400-6) are more sensitive to such inhibition.

The invention claimed is:
1. A compound selected from the group consisting of:

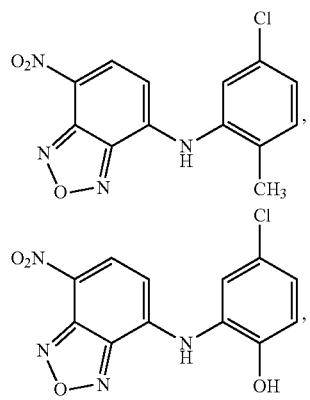

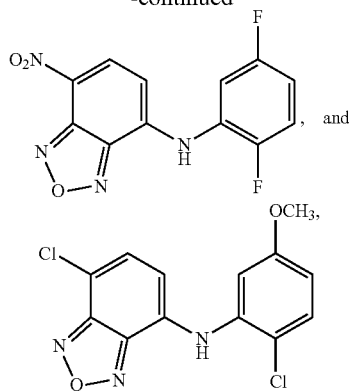, and

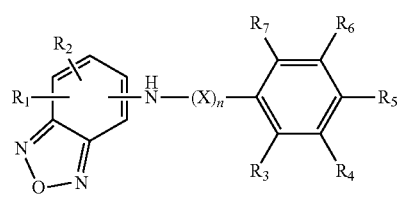

or a salt or solvate thereof.

2. A method of treating a p38 MAPK-regulated disease, said method comprising the administration to a patient in need of such a treatment a therapeutically effective amount of a compound of formula (I):

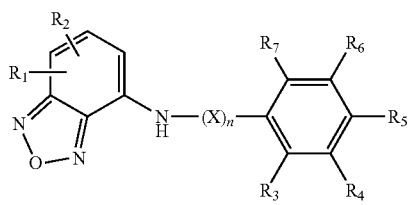 (I)

wherein
n represents 0 or 1;
X represents —CH$_2$— or —C(O)—;
R$_1$ and R$_2$ are independently selected from the group consisting of H, halogen, NO$_2$, CF$_3$ and CN;
R$_3$ and R$_6$ are independently selected from the group consisting of halogen, OH, optionally substituted C$_1$-C$_6$ alkyl, optionally substituted C$_1$-C$_6$ alkoxy, C$_{1-6}$ haloalkyl, NH$_2$, NO$_2$ and CN;
R$_4$, R$_5$ and R$_7$ are independently selected from the group consisting of H, halogen, OH, optionally substituted C$_1$-C$_6$ alkyl, optionally substituted C$_1$-C$_6$ alkoxy, C$_{1-6}$ haloalkyl, NH$_2$, NO$_2$ and CN;
or a salt or solvate thereof,
wherein the p38 MAPK-regulated disease is selected from an inflammatory disease, diabetes, obesity and pain.

3. The method according to claim 2, wherein the compound of formula (I) is a compound of formula (Ia):

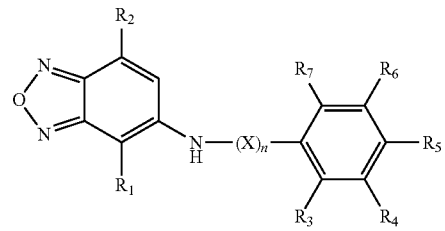 (Ia)

where n, X, R$_1$-R$_7$ are as defined in claim 2, or a salt or solvate thereof.

4. The method according to claim 2, wherein the compound of formula (I) is a compound of formula (Ib):

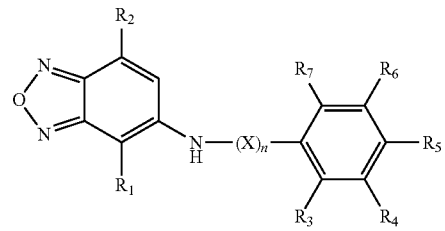 (Ib)

where n, X, R$_1$-R$_7$ are as defined in claim 2, or a salt or solvate thereof.

5. The method according to claim 3, wherein the compound of formula (Ia) is selected from the group consisting of:

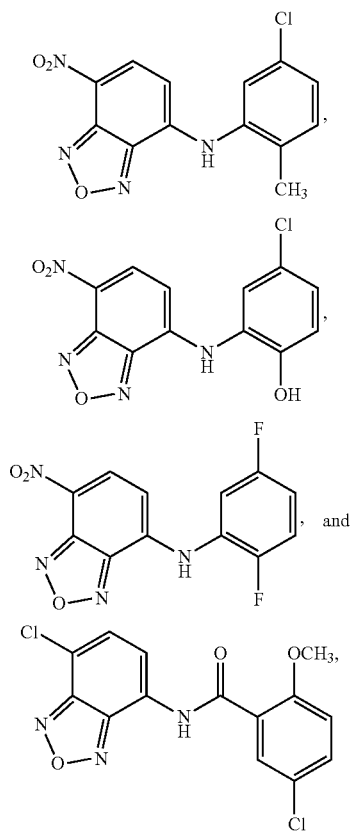

or a salt or solvate thereof.

6. The method according to claim 4, wherein the compound of formula (Ib) is selected from the group consisting of:

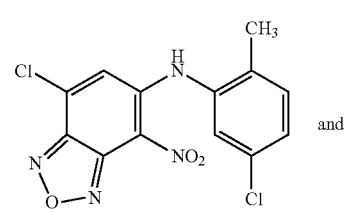 and

-continued

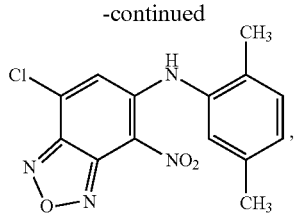

or a salt or solvate thereof.

7. The method according to claim 2, wherein the p38 MAPK regulated disease is an inflammatory disease or pain.

8. The method according to claim 7, wherein the pain is selected from inflammatory pain, neuropathic pain, pain associated with neurodegeneration and pain associated with multiple sclerosis.

9. A pharmaceutical composition comprising a compound as defined in claim 1, or a salt or solvate thereof, and a pharmaceutically acceptable carrier.

* * * * *